(12) United States Patent
Ganesan et al.

(10) Patent No.: US 11,213,391 B2
(45) Date of Patent: Jan. 4, 2022

(54) SYSTEMS AND METHODS FOR HEART VALVE THERAPY

(71) Applicant: Caisson Interventional, LLC, Maple Grove, MN (US)

(72) Inventors: Kavitha Ganesan, Minnetrista, MN (US); Ramji Iyer, Maple Grove, MN (US); Lucas T. Schneider, Champlin, MN (US); Todd J. Mortier, Mound, MN (US); Cyril J. Schweich, Jr., Maple Grove, MN (US)

(73) Assignee: Caisson Interventional, LLC, Maple Grove, MN (US)

( * ) Notice: Subject to any disclaimer, the term of this patent is extended or adjusted under 35 U.S.C. 154(b) by 245 days.

(21) Appl. No.: 15/957,154

(22) Filed: Apr. 19, 2018

(65) Prior Publication Data

US 2018/0338832 A1 Nov. 29, 2018

Related U.S. Application Data

(60) Provisional application No. 62/511,581, filed on May 26, 2017.

(51) Int. Cl.
*A61F 2/24* (2006.01)

(52) U.S. Cl.
CPC .......... *A61F 2/2439* (2013.01); *A61F 2/2409* (2013.01); *A61F 2/2418* (2013.01); *A61F 2/2436* (2013.01); *A61F 2220/0008* (2013.01); *A61F 2220/0033* (2013.01); *A61F 2230/005* (2013.01); *A61F 2230/0034* (2013.01); *A61F 2230/0039* (2013.01); *A61F 2230/0054* (2013.01); *A61F 2250/0039* (2013.01); *A61F 2250/0063* (2013.01)

(58) Field of Classification Search
CPC ...... A61F 2220/0008; A61F 2220/0033; A61F 2050/0063; A61F 2230/0034; A61F 2/2439; A61F 2/2409
See application file for complete search history.

(56) References Cited

U.S. PATENT DOCUMENTS

| 9,572,662 | B2* | 2/2017 | Morriss | A61F 2/2403 |
| 2007/0244552 | A1 | 10/2007 | Salahieh et al. | |
| 2010/0249915 | A1* | 9/2010 | Zhang | A61F 2/2436 |
| | | | | 623/2.11 |

(Continued)

FOREIGN PATENT DOCUMENTS

| WO | WO 2016/112085 | 7/2016 |
| WO | 2017/218375 A1 | 12/2017 |

OTHER PUBLICATIONS

International Search Report and Written Opinion in International Application No. PCT/US2018/028284, dated Jun. 27, 2018, 13 pages.

*Primary Examiner* — Sarah A Simpson
(74) *Attorney, Agent, or Firm* — Faegre Drinker Biddle & Reath LLP

(57) ABSTRACT

Prosthetic heart valves described herein can be deployed using a transcatheter delivery system and technique to interface and anchor in cooperation with the anatomical structures of a native heart valve. Deployment systems and methods for using the deployment systems described herein facilitate implanting a two-part prosthetic heart valve that is arranged in a nested configuration during the transcatheter delivery and deployment processes.

13 Claims, 15 Drawing Sheets

(56) References Cited

U.S. PATENT DOCUMENTS

2016/0113768 A1\* 4/2016 Ganesan ............... A61F 2/2403
                                                           623/2.17
2017/0042678 A1   2/2017 Ganesan et al.
2018/0296339 A1\* 10/2018 McLean ................ A61F 2/2439

\* cited by examiner

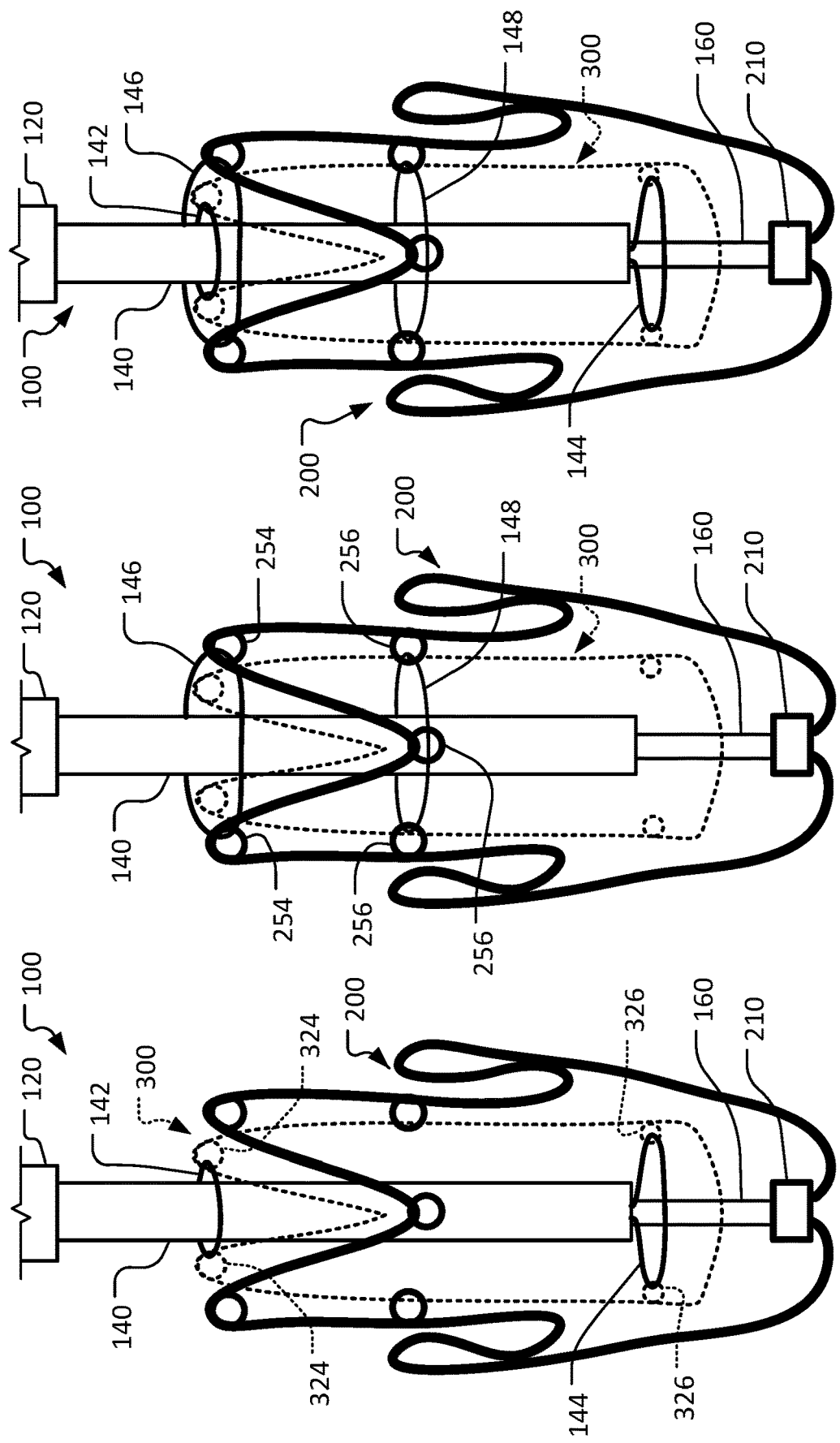

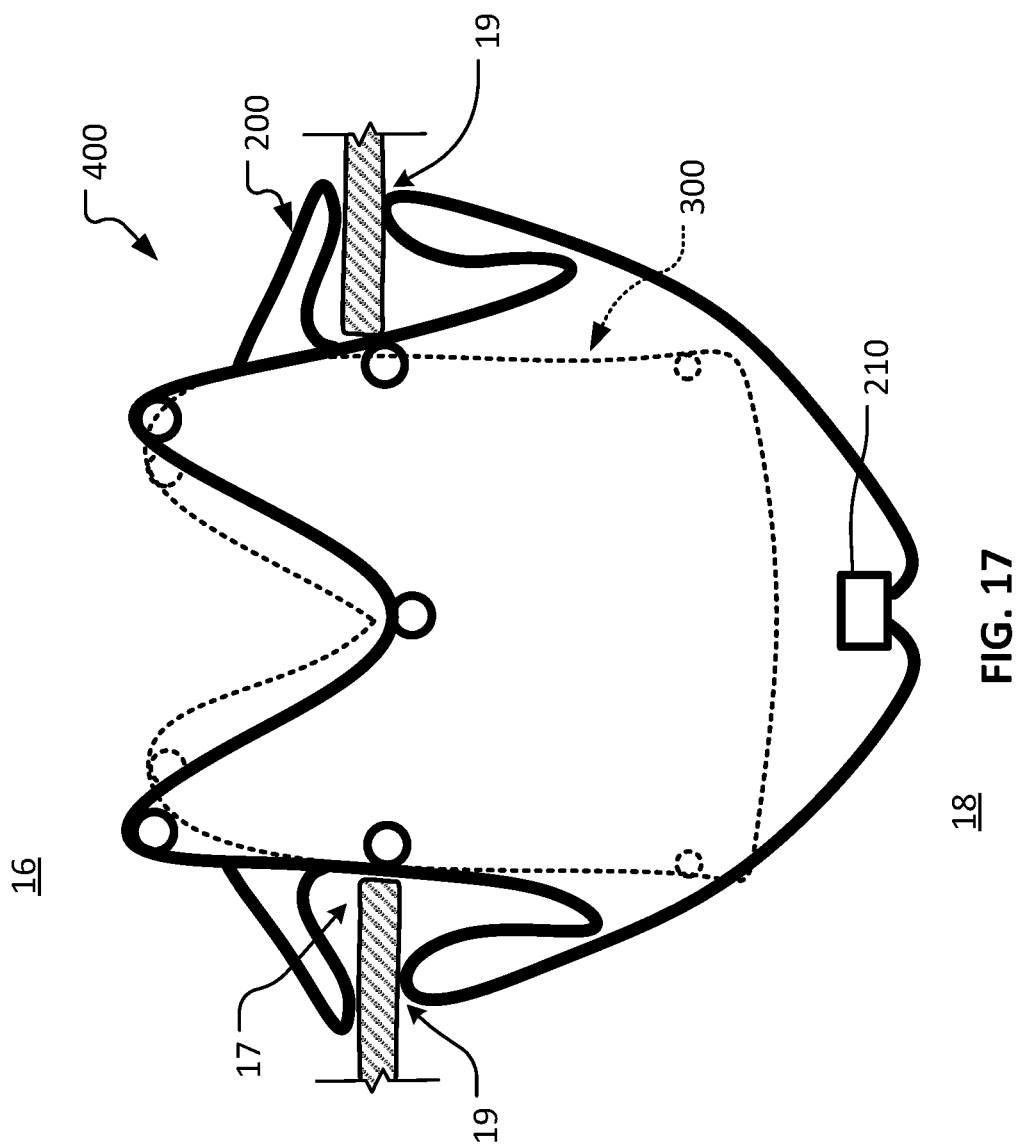

SYSTEMS AND METHODS FOR HEART VALVE THERAPY

CROSS-REFERENCE TO RELATED APPLICATIONS

This application claims the benefit of U.S. Provisional Ser. No. 62/511,581 filed May 26, 2017. The disclosure of the prior application is considered part of (and is incorporated by reference in) the disclosure of this application.

TECHNICAL FIELD

This document relates to prosthetic heart valves, such as prosthetic mitral valves that can be implanted using transcatheter techniques. This document also relates to systems and methods for implanting a two-part prosthetic heart valve that is arranged in a nested configuration during the transcatheter delivery and deployment processes.

BACKGROUND

The long-term clinical effect of valve regurgitation is recognized as a significant contributor to cardiovascular related morbidity and mortality. Thus, for many therapies intended to treat the mitral valve, one primary goal is to significantly reduce or eliminate regurgitation. By eliminating the regurgitation at the mitral valve, the destructive volume overload effects on the left ventricle can be attenuated. The volume overload of mitral regurgitation (MR) relates to the excessive kinetic energy required during isotonic contraction to generate overall stroke volume in an attempt to maintain forward stroke volume and cardiac output. It also relates to the pressure potential energy dissipation of the leaking valve during the most energy-consuming portion of the cardiac cycle, isovolumetric contraction. Additionally, therapies for MR reduction can have the effect of reducing the elevated pressures in the left atrium and pulmonary vasculature reducing pulmonary edema (congestion) and shortness of breath symptomatology. Such therapies for MR reduction may also have a positive effect on the filling profile of the left ventricle (LV) and the restrictive LV physiology that can result with MR. These pathophysiologic issues indicate the potential benefits of MR therapy, but also indicate the complexity of the system and the need for a therapy to focus beyond the MR level or grade.

In some percutaneous access procedures in which a medical device is introduced through a patient's skin and into a patient's blood vessel, such an access can be used to introduce devices into the patient without the use of large cut downs, which can be painful and in some cases can hemorrhage or become infected. A percutaneous access generally employs only a small hole through the skin, which subsequently seals relatively easily, and heals quickly in comparison to a surgical cut down.

SUMMARY

This document describes prosthetic heart valves, such as prosthetic mitral valves, that interface and anchor in cooperation with the anatomical structures of a native mitral valve. In addition, this document describes systems and methods for implanting a two-part prosthetic heart valve in which two expandable components are arranged in a nested configuration during both the transcatheter delivery process and the deployment process within the heart.

In one aspect, this disclosure is directed to a transcatheter mitral valve replacement system for a heart. The transcatheter mitral valve replacement system includes a delivery sheath having a distal end portion insertable into a left atrium, a delivery catheter slidably disposed within the delivery sheath, and a two-part prosthetic mitral valve coupled to the delivery catheter by one or more control wires. The two-part prosthetic mitral valve is configured to be disposed within the delivery sheath in a radially compressed condition and to radially self-expand when the two-part prosthetic mitral valve is outside of the delivery sheath and is unconstrained by the one or more control wires. The two-part prosthetic mitral valve includes a valve assembly including an expandable valve frame and a tri-leaflet occluder and an anchor assembly separately expandable from the valve assembly and defining an interior space within which the valve assembly is nested while the two-part prosthetic mitral valve is within the delivery sheath for simultaneous deployment from the delivery sheath.

Such a transcatheter mitral valve replacement system may optionally include one or more of the following features. The system may also include a pusher catheter slidably disposed within the deliver catheter and releasably coupled to the anchor assembly. The one or more control wires may include: a first control wire coupled to a proximal end portion of the anchor assembly; a second control wire coupled to a mid-body portion of the anchor assembly; a third control wire coupled to a proximal end portion of the valve assembly; and a fourth control wire coupled to a distal end portion of the valve assembly. The one or more control wires may include: a first control wire coupled to a proximal end portion of the anchor assembly; a second control wire coupled to a proximal end portion of the valve assembly; and a third control wire coupled to a distal end portion of the valve assembly. The one or more control wires may include: a first control wire coupled to a proximal end portion of the anchor assembly and to a proximal end portion of the valve assembly; a second control wire coupled to a mid-body portion of the anchor assembly; and a third control wire coupled to a distal end portion of the valve assembly. The one or more control wires may include: a first control wire coupled to a proximal end portion of the anchor assembly and to a proximal end portion of the valve assembly; and a second control wire coupled to a distal end portion of the valve assembly. A mid-body portion of the valve assembly may have a D-shaped cross-sectional shape. The anchor assembly may include four feet configured to reside within a sub-annular gutter of a native mitral valve when the two-part prosthetic mitral valve is implanted within the heart. The anchor assembly may include supra-annular features including an undulating supra-annular ring that defines an end of the interior space and atrial holding features configured to contact supra-annular tissue surfaces above an annulus of the mitral valve. The system may also include a deployment control system coupled to proximal ends of the delivery sheath and the delivery catheter. The deployment control system may include mechanisms for adjusting tension applied to the one or more control wires.

In another aspect, this disclosure is directed to a method for deploying a transcatheter prosthetic mitral valve system within a native mitral valve of a patient. The method may include: navigating a delivery sheath within the vasculature of the patient such that a distal end portion of the delivery sheath is positioned within a left atrium of the patient. The delivery sheath contains a two-part prosthetic mitral valve in a radially compressed condition and comprising: a valve assembly including an expandable valve frame and a tri-leaflet occluder; and an anchor assembly including an expandable anchor frame separate from the expandable valve frame of the valve assembly and defining an interior space within which the valve assembly is disposed while the two-part prosthetic mitral valve is within the delivery sheath. The method may also include expressing, in the left atrium, the two-part prosthetic mitral valve. A delivery catheter is releasably engaged with the two-part prosthetic mitral valve using one or more control wires. The valve assembly remains disposed within the interior space defined by the anchor assembly during and after the expressing. The method may also include engaging the anchor assembly with the native mitral valve. The anchor assembly is in a radially expanded condition while engaged with the native mitral valve. The method may also include, after the engaging the anchor assembly in in the radially expanded condition, expanding the valve assembly within the interior space to couple the valve assembly to the anchor assembly.

Such a method for deploying a transcatheter prosthetic mitral valve system within a native mitral valve of a patient may optionally include one or more of the following features. The expanding the valve assembly may include relieving tension of the one or more control wires to allow the valve assembly to self-expand. The engaging the anchor assembly with the native mitral valve may include relieving tension of the one or more control wires to allow the anchor assembly to self-expand and positioning four feet of the anchor assembly within a sub-annular gutter of the native mitral valve. The engaging the anchor assembly with the native mitral valve may also include positioning atrial holding features of the anchor assembly adjacent to supra-annular tissue surfaces above an annulus of the mitral valve.

In another aspect, this disclosure is directed to a two-part prosthetic heart valve having two separately expandable components arranged in a nested configuration for transcatheter delivery to a heart. The two-part prosthetic heart valve includes an anchor assembly including an expandable anchor frame defining an interior space and defining a plurality of sub-annular anchor feet. The anchor assembly is expandable from a compressed anchor delivery configuration to an expanded anchor deployment configuration in which the sub-annular anchor feet are sized and shaped to engage along an underside of a mitral valve annulus. The two-part prosthetic heart valve also includes a valve assembly including an expandable valve frame that is separately expandable from the expandable anchor frame. The valve assembly is nested within the interior space of the expandable anchor frame while the anchor assembly is in the compressed anchor delivery configuration. The expandable valve frame defines a central orifice and a leaflet occluder positioned within the central orifice. The valve assembly is expandable from a compressed valve delivery configuration to an expanded valve deployment configuration after the anchor assembly is in the expanded anchor deployment configuration.

Such a two-part prosthetic heart valve may optionally include one or more of the following optional features. The plurality of sub-annular anchor feet of the anchor assembly may include four anchor feet configured to reside within a sub-annular gutter of a native mitral valve when the anchor assembly is in the expanded anchor deployment configuration. The anchor assembly may include a supra-annular element including an undulating supra-annular ring that defines an uppermost end of the interior space and atrial holding elements configured to contact supra-annular tissue above the mitral valve annulus.

In another aspect, this disclosure is directed to a method of deploying a two-part prosthetic heart valve having two separately expandable components arranged in a nested configuration during transcatheter delivery to a heart. The method includes delivering a valve assembly having an expandable valve frame to the heart while nested within a separately expandable anchor frame of an anchor assembly in a compressed anchor delivery configuration, and contemporaneously deploying the valve assembly and the anchor assembly into the heart while the valve assembly is nested within the anchor assembly.

Such a method of deploying a two-part prosthetic heart valve having two separately expandable components arranged in a nested configuration during transcatheter delivery to a heart may optionally include one or more of the following features. The method may also include expanding the anchor assembly from the compressed anchor delivery configuration to an expanded anchor deployment configuration in which sub-annular anchor feet of the anchor assembly engage along an underside of a mitral valve annulus. The method may also include, after expanding the anchor assembly to the expanded anchor deployment configuration, expanding the valve assembly from a compressed valve configuration to an expanded valve deployment configuration in which the valve assembly mechanically mates to an interior region of the anchor assembly.

Some or all of the embodiments described herein may provide one or more of the following advantages. First, using the devices, systems, and methods described herein, various medical conditions, such as heart valve conditions, can be treated in a minimally invasive fashion. Such minimally invasive techniques can tend to reduce recovery times, patient discomfort, and treatment costs.

Second, the devices, systems, and methods described herein facilitate the implantation of a two-part prosthetic heart valve in which two expandable components are arranged in a nested configuration during the transcatheter delivery and deployment processes. Accordingly, the time to complete the procedure is advantageously minimized. This can result in reduced time in the operating room, lessened patient risks, and lower procedural costs.

Third, the transcatheter prosthetic heart valve and deployment systems described herein are configured to facilitate accurate control of the prosthetic valve components during the delivery and deployment process. In some embodiments, one or more control wires are coupled to end portions or middle portions of the prosthetic valve components in a manner that allows for isolated, accurate movements of each degree of freedom associated with the catheters and prosthetic valve components. Accordingly, relatively complex catheter and/or valve component movements are facilitated in an accurately controllable and user-convenient manner. In result, transcatheter implant procedures can be performed with enhanced patient safety and treatment efficacy using the devices, systems, and methods described herein.

Fourth, some embodiments of the prosthetic mitral valve and deployment systems described herein can be used in a completely percutaneous/transcatheter mitral replacement procedure that is streamlined, safe, reliable, and repeatable by surgeons and/or interventional cardiologists of a variety of different skill levels.

Fourth, in particular embodiments, the two-part prosthetic mitral valve can optionally include two different expandable components (e.g., an anchor assembly and a valve assembly) that are delivered to the implantation site in a nested arrangement. For example, the first component (e.g., the anchor assembly including a first expandable frame) can be configured to engage with the heart tissue that is at or proximate to the annulus of the native mitral valve, and the second component (e.g., the valve assembly including a second expandable frame) can be configured to provide a seal interface with native valve leaflets of the mitral valve.

Fifth, using the systems and methods for implanting a two-part prosthetic heart valve that is arranged in a nested configuration during the transcatheter delivery and deployment processes, patients can be treated while guarding the patients' hemodynamic stability during the implantation process. Such devices and techniques can tend to reduce the need for ancillary interventions, such as the need for installing a balloon pump and the like.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 7 schematically depicts the nested two-part prosthetic valve as in FIG. 6, with the addition of control wires coupled to the valve assembly.

FIG. 8 schematically depicts the nested two-part prosthetic valve as in FIG. 6, with the addition of control wires coupled to the anchor assembly.

FIG. 9 schematically depicts the nested two-part prosthetic valve as in FIG. 6, with the addition of control wires coupled to the valve assembly and to the anchor assembly.

FIG. 17 schematically depicts the nested two-part prosthetic valve as in FIG. 16, fully deployed with the delivery catheters detached from the prosthetic valve and removed from the area of the native valve.

Like reference symbols in the various drawings indicate like elements.

DETAILED DESCRIPTION OF ILLUSTRATIVE EMBODIMENTS

This document describes prosthetic heart valves, such as prosthetic mitral valves, that interface and anchor in cooperation with the anatomical structures of a native mitral valve. In addition, this document describes systems and methods for implanting a two-part prosthetic heart valve in which two expandable components are arranged in a nested configuration during the transcatheter delivery and deployment processes.

Figure 1:
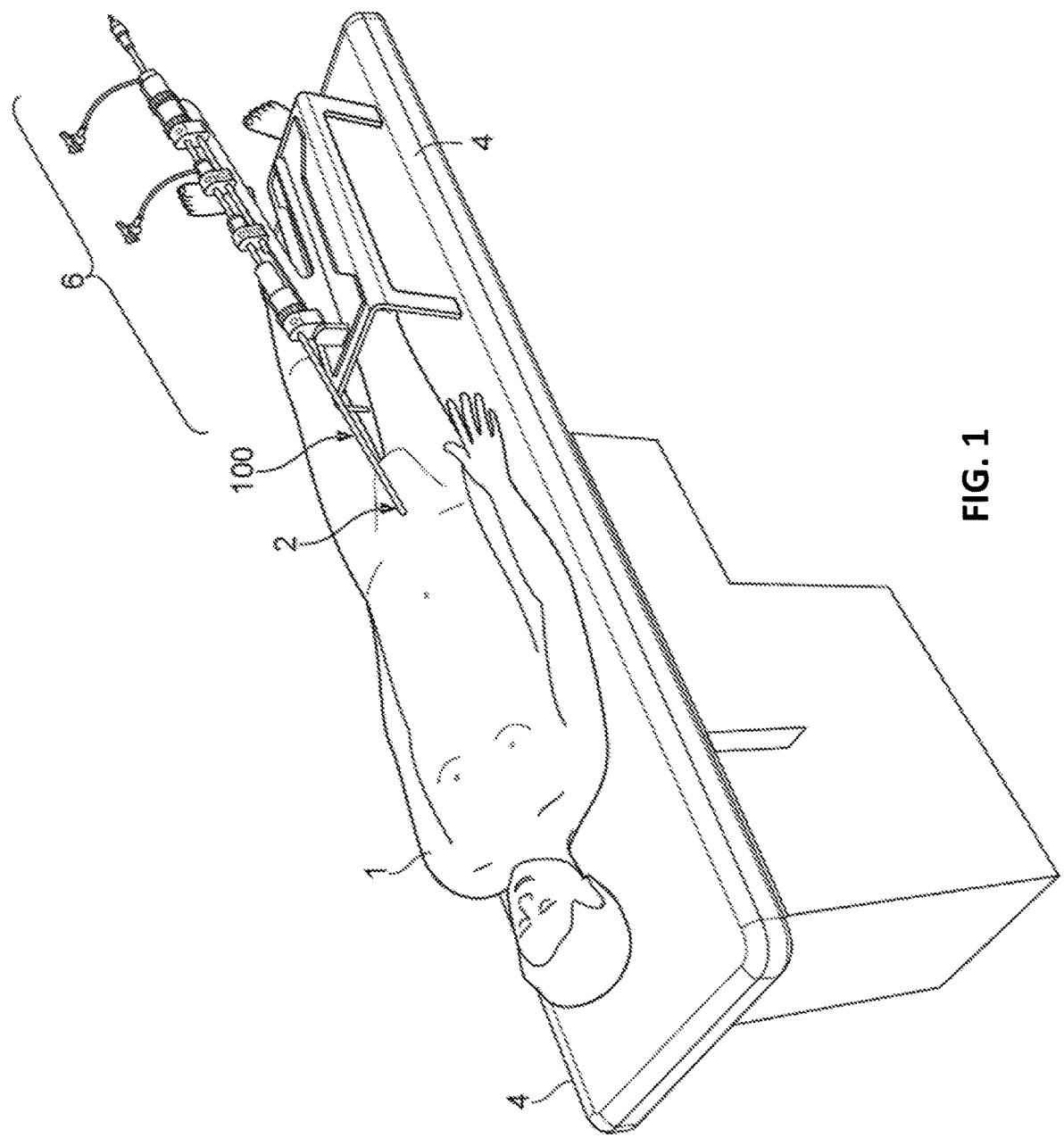
FIG. 1 shows a perspective view of a patient on an operating table undergoing a percutaneous deployment of an implantable prosthetic heart valve in accordance with some embodiments.
Figure 2:
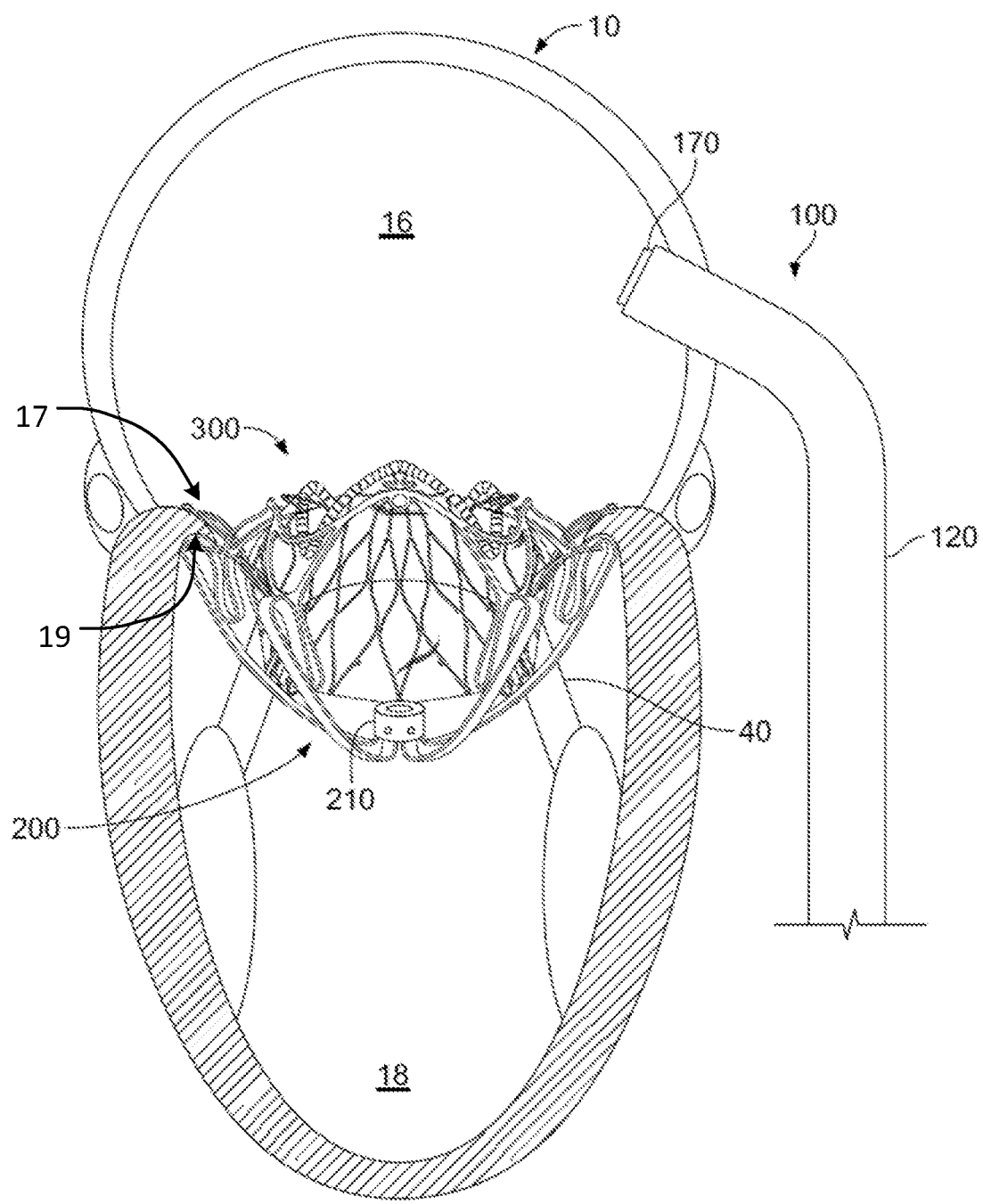
FIG. 2 shows a commissural cross-sectional view of a human heart (from the left side of the heart) with a two-part prosthetic valve assembly deployed within a native mitral valve of the heart.
Figure 3:
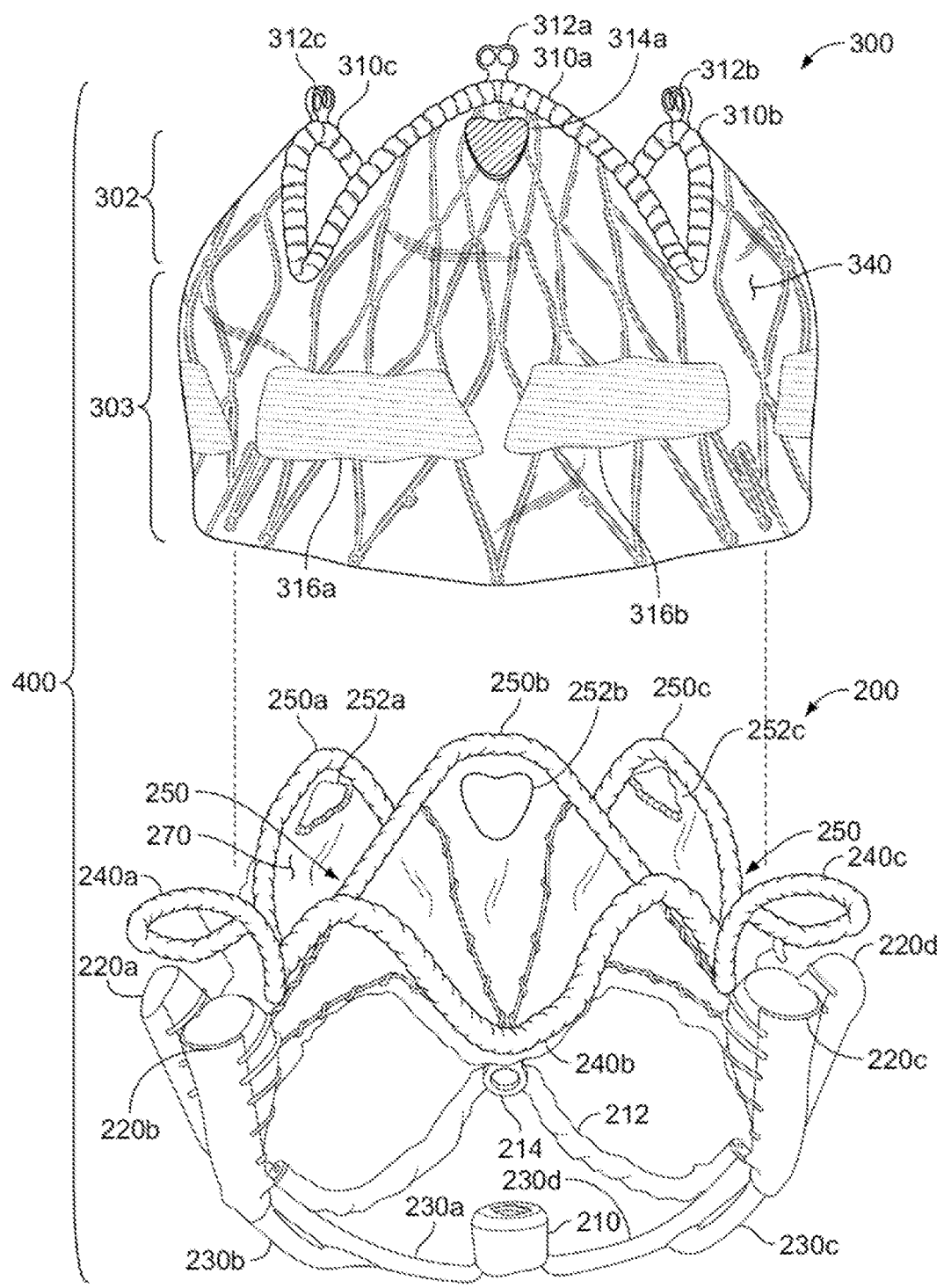
FIG. 3 is an exploded posterior side view of the two-part prosthetic valve assembly of FIG. 2, showing an example anchor assembly and an example valve assembly, in accordance with some embodiments.

Referring to FIGS. 1-3, in some therapeutic medical procedures a two-part prosthetic mitral valve 400 can be deployed in a patient 1 using a transcatheter delivery system 100. In some implementations, the prosthetic mitral valve 400 is percutaneously deployed via a femoral or iliac vein through a groin opening/incision 2 in the patient 1 in a minimally invasive fashion. In particular implementations, a deployment control system 6 is used to initiate and/or control the movements of various components of the transcatheter delivery system 100, and of the prosthetic mitral valve 400, as described further below.

The two-part prosthetic mitral valve 400 can be delivered to and implanted in the heart 10 using a percutaneous, or minimally invasive, technique via the venous or arterial system (without open-chest or open-heart surgery). In some implementations, the transcatheter delivery system 100 and prosthetic mitral valve 400 are used in conjunction with one or more imaging modalities such as x-ray fluoroscopy, echocardiography, magnetic resonance imaging, computed tomography (CT), and the like. Accordingly, various components of the transcatheter delivery system 100 and/or the prosthetic mitral valve 400 can include one or more features to enhance their visibilities under imaging modalities, such as radio-opaque markers.

Early steps of the process for deploying the two-part prosthetic mitral valve 400 includes the placement of a guidewire 110 (refer to FIG. 14) within the vasculature and heart 10 of the patient 1. In the depicted implementation, the guidewire 110 is installed into the heart 10 prior to the other components of the delivery system 100. In some embodiments, the guidewire 110 has a diameter of about 0.035 inches (about 0.89 mm). In some embodiments, the guidewire 110 has a diameter in a range of about 0.032 inches to about 0.038 inches (about 0.8 mm to about 0.97 mm). In some embodiments, the guidewire 110 has a diameter smaller than 0.032 inches (about 0.80 mm) or larger than 0.038 inches (about 0.97 mm). In some embodiments, the guidewire 110 is made of materials such as, but not limited to, nitinol, stainless steel, high-tensile-strength stainless steel, and the like, and combinations thereof. The guidewire 110 may include various tip designs (e.g., J-tip, straight tip, etc.), tapers, coatings, covers, radiopaque (RO) markers, and other features. In some embodiments, the guidewire 110 has one or more portions with differing lateral stiffnesses, column strengths, lubricity, and/or other physical properties in comparison to other portions of the guidewire 110.

In some implementations, the guidewire 110 is percutaneously inserted into a femoral vein of the patient 1. The guidewire 110 is routed to the inferior vena cava and into the right atrium. After creating an opening in the atrial septum (e.g., a trans-septal puncture of the fossa ovalis or other portion of the atrial septum), the guidewire 110 is routed into the left atrium 16. Lastly, the guidewire 110 is routed through the mitral valve 17 and into the left ventricle 18. This is preferably performed without entangling the guidewire 110 with the chordae tendineae 40 of the mitral valve 17. In some implementations, the guidewire 110 can be installed into the heart 10 along other anatomical pathways. The guidewire 110 thereafter serves as a rail over which other components of the delivery system 100 are passed.

The transcatheter delivery system 100 facilitates implantation of the two-part prosthetic mitral valve 400 in the heart 10 while the heart 10 is beating. Using interventional cardiology techniques, the transcatheter prosthetic heart valve delivery system 100 can be navigated through the venous vasculature of the patient 1, and through the atrial septum (e.g., a trans-septal puncture of the fossa ovalis or other portion of the atrial septum), to obtain access to the left atrium 16 of the patient's heart 10. FIG. 2 shows the two-part prosthetic mitral valve 400 fully deployed within the native mitral valve such that the prosthetic mitral valve 400 is performing the mitral valve function.

In the depicted embodiment, the example two-part prosthetic mitral valve 400 includes an anchor assembly 200 (including a first expandable frame structure) and a separate valve assembly 300 (including a second expandable frame structure). The valve assembly 300 is sized and shaped to releasably mount to the framework of the anchor assembly 200.

In the depicted embodiment, the anchor assembly 200 includes four anchor feet: a lateral anterior foot 220a, a lateral posterior foot 220b, a medial posterior foot 220c, and a medial anterior foot 220d. In some embodiments, fewer or more anchor feet may be included (e.g., two, three, five, six, or more than six). In some embodiments, the anchor feet 220a, 220b, 220c, and 220d are portions of the anchor assembly 200 that are configured for contact with a sub-annular gutter 19 of the native mitral valve 17, without penetrating tissue of the native mitral valve 17. Accordingly, the anchor feet 220a, 220b, 220c, and 220d have atraumatic surfaces that are generally comparable to feet. However, in some embodiments one or more of the anchor feet 220a, 220b, 220c, and 220d are configured to penetrate tissue and may have anchor features such as barbs, coils, hooks, and the like.

It should be understood that the depicted anchor assembly 200 is merely one non-limiting example of the anchor assemblies included within the scope of this disclosure.

In some embodiments, the anchor assembly 200 includes supra-annular structures and sub-annular structures. For example, in some embodiments the sub-annular structures of the anchor assembly 200 can include the aforementioned anchor feet 220a, 220b, 220c, and 220d, a systolic anterior motion (SAM) containment member 212, and a hub 210. The SAM containment member 212 is designed to inhibit the incursion of an anterior leaflet of the native mitral valve into the LVOT during systole, which might otherwise cause LVOT obstruction or the creation of high LVOT pressure gradients. In some embodiments, the hub 210 functions as a connection structure for the delivery system 100. In addition, the hub 210 can function as a stabilizing structural component from which a lateral anterior sub-annular support arm 230a and a medial anterior sub-annular support arm 230d extend to the anchor feet 220a and 220d respectively. In some embodiments, a lateral posterior sub-annular support arm 230b extends from the lateral anterior sub-annular support arm 230a to the lateral posterior foot 220b. In some embodiments, a medial posterior sub-annular support arm 230c extends from the medial anterior sub-annular support arm 230d to the medial posterior foot 220c.

In the depicted embodiment, the supra-annular structures of the anchor assembly 200 include: a lateral anterior atrial holding feature 240a, a posterior atrial holding feature 240b, and a medial anterior atrial holding feature 240c; a lateral anterior anchor arch 250a, a posterior anchor arch 250b, and a medial anterior anchor arch 250c. The lateral anterior anchor arch 250a, the posterior anchor arch 250b, and the medial anterior anchor arch 250c are joined with each other to form an undulating supra-annular ring 250 that acts as a supra-annular structural element for the anchor assembly 200. The supra-annular ring 250 also defines an opening to a space within the interior of the anchor assembly 200 that is configured to receive and engage with the valve assembly 300. The atrial holding features 240a, 240b, and 240c are configured to contact the shelf-like supra-annular tissue surface above the mitral valve annulus, and to thereby stabilize the anchor assembly 200 in supra-annular areas and to provide migration resistance in the direction towards the left ventricle 18.

The valve assembly 300 includes a proximal end portion 302 and a distal end portion 303. When the valve assembly 300 is implanted in a native mitral valve, the proximal end portion 302 is located supra-annular (in the left atrium 16) and the distal end portion 303 is located sub-annular (in the left ventricle 18). The proximal end portion 302 defines the generally circular entrance orifice of the valve assembly 300. At least three prosthetic valve leaflets (not visible) are located within the valve assembly 300.

It should be understood that the depicted valve assembly 300 is merely one non-limiting example of the valve assemblies included within the scope of this disclosure.

In the depicted embodiment, the valve assembly 300 generally flares outward along a distal direction. Said differently, the distal end portion 303 is flared outward in comparison to the proximal end portion 302. Accordingly, the proximal end portion 302 defines a smaller outer profile in comparison to the distal end portion 303. However, some regions of the distal end portion 303 bow inwardly. Such inward bowing can serve to mitigate LVOT obstructions and enhance sealing in some cases.

In some embodiments, the periphery of the distal end portion 303 is generally D-shaped in cross-section. The D-shaped periphery of the distal end portion 303 provides the valve assembly 300 with an advantageous outer profile for interfacing and sealing with the native mitral valve. For example, in some implementations sealing is attained by coaptation between the D-shaped periphery of the distal end portion 303 and the leaflets of the native mitral valve.

In the depicted embodiment, the proximal end portion 302 of the valve assembly 300 includes three atrial leaflet arches 310a, 310b, and 310c that together define an undulating ring at the proximal end portion 302. Each of the leaflet arches 310a, 310b, and 310c includes an apex having one or more holes 312a, 312b, and 312c respectively. In some embodiments, the holes 312a, 312b, and 312c are used for coupling the proximal end of the valve assembly 300 to a delivery catheter using a proximal control wire. In some embodiments, one or more of the holes 312a, 312b, and 312c are used for containing radiopaque material.

In some embodiments, such as the depicted embodiment, valve assembly 300 includes three leaflets (not visible) that perform the occluding function of the prosthetic mitral valve 400. The cusps of the three leaflets are fixed to the three atrial leaflet arches 310a, 310b, and 310c, and to three commissural posts (not visible) that each extend distally from the intersections of the three leaflet arches 310a, 310b, and 310c. In some embodiments, the three commissural posts are disposed at about 120° apart from each other. The commissural posts each have a series of holes that can be used for attachment of the prosthetic valve leaflets, such as by suturing. The three leaflet arches 310a, 310b, and 310c and the three commissural posts are areas on the valve assembly 300 to which the three prosthetic valve leaflets become attached to comprise a tri-leaflet occluder. As such, the valve assembly 300 provides a proven and advantageous frame configuration for the tri-leaflet occluder. When implanted in the native mitral valve 17, the tri-leaflet occluder of the valve assembly 300 provides open flow during diastole and occlusion of flow during systole. The free edges of the three leaflets can seal by coaptation with each other during systole and open during diastole.

The three leaflets can be comprised of natural or synthetic materials. For example, the three leaflets can be comprised of any of the materials described below in reference to the coverings 270 and/or 340, including the natural tissues such as, but not limited to, bovine, porcine, ovine, or equine pericardium. In some such embodiments, the tissues are chemically cross-linked using glutaraldehyde, formaldehyde, or triglycidyl amine solution, or other suitable cross-linking agents. In some embodiments, the leaflets have a thickness in a range of about 0.005" to about 0.020" (about 0.13 mm to about 0.51 mm), or about 0.008" to about 0.012" (about 0.20 mm to about 0.31 mm). In some embodiments, the leaflets have a thickness that is less than about 0.005" (about 0.13 mm) or greater than about 0.020" (about 0.51 mm).

In some embodiments, the occluding function of the prosthetic mitral valve 400 can be performed using configurations other than a tri-leaflet occluder. For example, bi-leaflet, quad-leaflet, or mechanical valve constructs can be used in some embodiments.

As shown in FIG. 3, in some embodiments the anchor assembly 200 includes a covering material 270 disposed on one or more portions of the anchor assembly 200 and/or the valve assembly 300 includes a covering material 340 disposed on one or more portion of the valve assembly 300. The covering materials 270/340 can provide various benefits. For example, in some implementations the covering materials 270/340 can facilitate tissue ingrowth and/or endothelialization, thereby enhancing the migration resistance of the anchor assembly 200 and/or valve assembly 300, and preventing thrombus formation on blood contact elements. In another example, as described further below, the covering materials 270/340 can be used to facilitate coupling between the anchor assembly 200 and the valve assembly 300 that is received therein. The cover materials 270/340 also prevent or minimizes abrasion and/or fretting between the anchor assembly 200 and valve assembly 300 to enhance durability. The covering materials 270/340 are omitted in FIG. 2 to provide enhanced visualization of the interface between the anchor assembly 200 and valve assembly 300 with the native mitral valve 17.

In some embodiments, the covering materials 270/340, or portions thereof, comprises a fluoropolymer, such as an expanded polytetrafluoroethylene (ePTFE) polymer. In some embodiments, the covering materials 270/340, or portions thereof, comprises a polyester, a silicone, a urethane, ELAST-EON™ (a silicone and urethane polymer), another biocompatible polymer, DACRON®, polyethylene terephthalate (PET), copolymers, or combinations and sub-combinations thereof. In some embodiments, the covering materials 270/340, or portions thereof, comprises a biological tissue. For example, in some embodiments the covering materials 270/340 can include natural tissues such as, but not limited to, bovine, porcine, ovine, or equine pericardium. In some such embodiments, the tissues are chemically treated using glutaraldehyde, formaldehyde, or triglycidylamine (TGA) solutions, or other suitable tissue crosslinking agents.

In some embodiments, the anchor assembly 200 can include features that are designed for mechanically mating with the valve assembly 300 that is received by the anchor assembly 200. For example, the lateral anterior anchor arch 250a, the posterior anchor arch 250b, and the medial anterior anchor arch 250c can be shaped and arranged for coupling with the valve assembly 300. In addition, in some embodiments the anchor arches 250a, 250b, and 250c can include one or more covering-material cut-outs 252a, 252b, and 252c respectively. In some embodiments, the valve assembly 300 can include a fabric portion 314a (and fabric portions 314b and 314b; not visible) that become physically disposed within the covering-material cut-outs 252a, 252b, and 252c when the valve assembly 300 is coupled with the anchor assembly 200. Such an arrangement can serve to provide a robust coupling arrangement between the valve assembly 300 and the anchor assembly 200.

In some embodiments, the expandable frame structure of the anchor assembly 200 and/or the expandable frame structure of the valve assembly 300 are formed from a single piece of precursor material (e.g., sheet or tube) that is cut and expanded (and then connected to the hub 210 in the case of the anchor assembly 200). For example, some embodiments are fabricated from a tube that is laser-cut (or machined, chemically etched, water-jet cut, etc.) and then expanded and heat-set into its final expanded size and shape. In some embodiments, the expandable frame structure of the anchor assembly 200 is created compositely from multiple elongate members (e.g., wires or cut members) that are joined together with the hub 210 and each other to form the anchor assembly 200.

The expandable frame structure of the anchor assembly 200 and/or the expandable frame structure of the valve assembly 300 can comprise various materials and combinations of materials. In some embodiments, nitinol (NiTi) is used as the material of the elongate members of the expandable frame structure of the anchor assembly 200 and/or the valve assembly 300, but other materials such as stainless steel, L605 steel, polymers, MP35N steel, stainless steels, titanium, cobalt/chromium alloy, polymeric materials, Pyhnox, Elgiloy, or any other appropriate biocompatible material, and combinations thereof can be used. The superelastic properties of NiTi make it a particularly good candidate material for the elongate members of the expandable frame structure of the anchor assembly 200 and/or the valve assembly 300 because, for example, NiTi can be heat-set into a desired shape. That is, NiTi can be heat-set so that the anchor assembly 200 and/or the valve assembly 300 tends to self-expand into a desired shape when the anchor assembly 200 and/or the valve assembly 300 is unconstrained, such as when the anchor assembly 200 and/or the valve assembly 300 is deployed out from the anchor delivery sheath 130. An expandable frame structure of the anchor assembly 200 and/or the valve assembly 300 made of NiTi, for example, may have a spring nature that allows the anchor assembly 200 and/or the valve assembly 300 to be elastically collapsed or "crushed" to a low-profile delivery configuration and then to self-expand to the expanded configuration. The anchor assembly 200 and/or the valve assembly 300 may be generally conformable, fatigue resistant, and elastic to conform to the topography of the surrounding tissue when the anchor assembly 200 and/or the valve assembly 300 is deployed in the native mitral valve 17 of the patient 1.

Still referring to FIGS. 1-3, the anchor feet 220a, 220b, 220c, and 220d are sized and shaped to engage the sub-annular gutter 19 of the mitral valve 17. In some embodiments, the anterior feet 220a and 220d are spaced apart from each other by a distance in a range of about 30 mm to about 45 mm, or about 20 mm to about 35 mm, or about 40 mm to about 55 mm. In some embodiments, the posterior feet 220b and 220c are spaced apart from each other by a distance in a range of about 20 mm to about 30 mm, or about 10 mm to about 25 mm, or about 25 mm to about 40 mm.

In some embodiments, the anchor feet 220a, 220b, 220c, and 220d have a height ranging from about 8 mm to about 12 mm, or more than about 12 mm. In some embodiments, the anchor feet 220a, 220b, 220c, and 220d have a gutter engaging surface area (when fabric covered) ranging from about 6 mm$^2$ to about 24 mm$^2$. In some embodiments, the anchor feet 220a, 220b, 220c, and 220d each have essentially the same gutter engaging surface area. In particular embodiments, one or more of the anchor feet 220a, 220b, 220c, and 220d has a different gutter engaging surface area than one or more of the other anchor feet 220a, 220b, 220c, and 220d. The anchor feet 220a, 220b, 220c, and 220d can have widths ranging within about 1.5 mm to about 4.0 mm or more, and lengths ranging within about 3 mm to about 6 mm or more. The anchor feet 220a, 220b, 220c, and 220d are sized and shaped so that the anchor assembly 200 does not significantly impair the natural function of mitral valve chordae tendineae 40, the native mitral valve leaflets, and papillary muscles even after the anchor assembly 200 is anchored at the mitral valve site.

Figure 4:
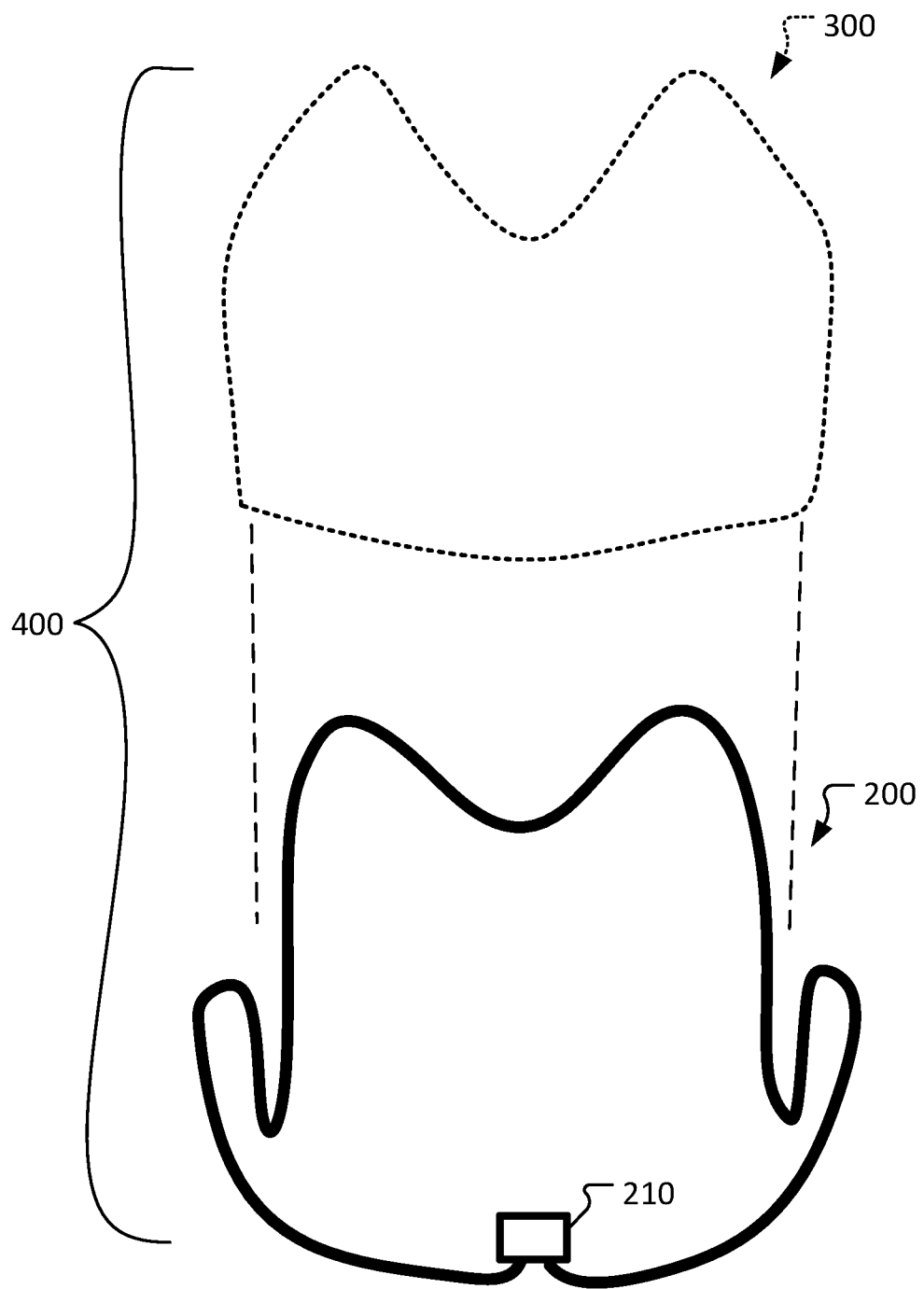
FIG. 4 is a simplified, schematic representation of FIG. 3, including the anchor assembly and the valve assembly depicted in an exploded view.

Referring to FIG. 4, the two-part prosthetic mitral valve 400 can be schematically depicted (e.g., shown here in an exploded view corresponding to FIG. 3) to make the transcatheter deployment technique described below easier to visualize and understand. As described above, the two-part prosthetic mitral valve 400 includes the anchor assembly 200 (including the hub 210) and the valve assembly 300. The valve assembly 300 is removably receivable within the interior space of the anchor assembly 200 as described above. In this figure (and in FIGS. 5-13 and 15-17), the anchor assembly 200 is schematically shown in solid lines, while the valve assembly 300 is schematically shown in dashed lines for illustrative purposes. Those different line types (solid lines and dashed lines) are being used solely to help the viewer clearly distinguish the anchor assembly 200 from the valve assembly 300. The use of the solid lines and dashed lines in this figure (and in FIGS. 5-13 and 15-17) is provided for clarity of viewing of the two assemblies 200 and 300 in the nested arrangement, but the use of the dashed lines in this figure (and in FIGS. 5-13 and 15-17) does not necessarily mean the elements shown in dashed lines are hidden or concealed from view.

Figure 5:
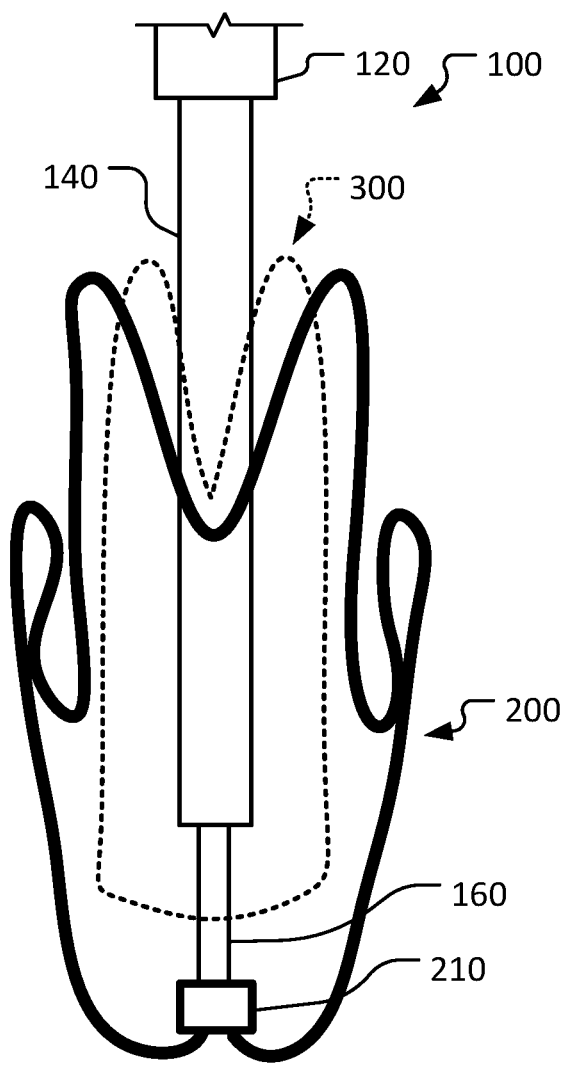
FIG. 5 schematically depicts the anchor assembly and the valve assembly of the two-part prosthetic valve in a nested arrangement and after the two-part valve has emerged from a delivery sheath.

Referring to FIG. 5, in some implementations the valve assembly 300 is positioned within the anchor assembly 200 during the transcatheter delivery and deployment processes. The two devices (e.g., the anchor assembly 200 and the valve assembly 300) can be separate devices having different frame structures that are independently expandable from one another, but with one device laterally surrounding the other device so that when they are radially expanded in situ, the anchor assembly 200 and the valve assembly 300 will be mechanically mated together. As such, the two-part prosthetic heart valve 400 includes two expandable components that are arranged in a nested configuration during both the transcatheter delivery process and the deployment process within the heart.

In some implementations, a sheath 120 (which is a part of the transcatheter delivery system 100) can be used to simultaneously deliver the anchor assembly 200 and the valve assembly 300 to the heart 10. That is, the anchor assembly 200 and the valve assembly 300 can be elastically collapsed to reduced diameters and constrained within the confines of the low-profile sheath 120. In that arrangement, the sheath 120 (containing the anchor assembly 200 and the valve assembly 300 in radially collapsed configurations) can be navigated through the patient's vasculature and heart to arrive at the target location (e.g., within the heart proximate to the patient's native mitral valve). There, the anchor assembly 200 and the valve assembly 300 can be expressed out of the sheath 120. FIG. 5 depicts the anchor assembly 200 and the valve assembly 300 after having been expressed from the sheath 120. As shown in this embodiment, the valve assembly 300 is nested within the anchor assembly 200.

In some embodiments the sheath 120 has an outer diameter of about 28 Fr (about 9.3 mm), or about 30 Fr (about 10.0 mm). In some embodiments, the sheath 120 has an outer diameter in the range of about 26 Fr to about 34 Fr (about 8.7 mm to about 11.3 mm). In some embodiments, the sheath 120 has an outer diameter in the range of about 20 Fr to about 28 Fr (about 6.7 mm to about 9.3 mm).

The transcatheter delivery system 100 can also include a delivery catheter 140. As described further below, the anchor assembly 200 and the valve assembly 300 can be attached to the delivery catheter 140 using one or more control wires. The delivery catheter 140 can thereby control the positioning of the anchor assembly 200 and the valve assembly 300 relative to the sheath 120. For example, the delivery catheter 140 can be pushed distally while the sheath 120 is held stationary to make the anchor assembly 200 and the valve assembly 300 emerge from within the sheath 120. Or, the sheath 120 can be pulled proximally while the delivery catheter 140 is held stationary to make the anchor assembly 200 and the valve assembly 300 emerge from within the sheath 120.

The transcatheter delivery system 100 can also include an inner catheter 160 (also referred to herein as a "pusher catheter 160"). In some implementations, the inner catheter 160 is releasably coupled with the hub 210 of the anchor assembly 200. For example, a distal end portion of the inner catheter 160 can be threadedly coupled with the hub 210. When the nested anchor assembly 200 and valve assembly 300 are expressed from the sheath 120, the inner catheter 160 can be moved (e.g., pushed distally) or held stationary in concert with the delivery catheter 140.

In some embodiments, components of the transcatheter delivery system 100 (such as the sheath 120, the delivery catheter 140, and/or the inner catheter 160) can include one or more of the following features. In some embodiments, one or more portions of the components of the transcatheter delivery system 100 are steerable (also referred to herein as "deflectable"). Using such steering, the transcatheter delivery system 100 can be deflected to navigate the patient's anatomy and/or to be positioned in relation to the patient's anatomy as desired. For example, the sheath 120 can be angled within the right atrium 12 to navigate the sheath 120 from the inferior vena cava 11 to the atrial septum. Accordingly, in some embodiments the sheath 120 may include at least one deflectable zone. Using a device such as the deployment control system 6 (FIG. 1) a clinician can controllably deflect the deflection zone of the sheath 120 (and/or other components of the transcatheter delivery system 100) as desired. In some embodiments, one or more components of the transcatheter delivery system 100 can include one or more portions that have differing properties as compared to other portions of the component. For example, a component such as the sheath 120, the delivery catheter 140, and/or the inner catheter 160 may have a portion that has greater flexibility, stiffness, column strength, and/or the like as compared to other portions of that same component.

In some embodiments, the sheath 120, the delivery catheter 140, and/or the inner catheter 160 can comprise a tubular polymeric or metallic material. For example, in some embodiments the sheath 120, the delivery catheter 140, and/or the inner catheter 160 can be made from polymeric materials such as, but not limited to, polytetrafluoroethylene (PTFE), fluorinated ethylene propylene (FEP), HYTREL®, nylon, PICOFLEX®, PEBAX®, TECOFLEX®, and the like, and combinations thereof. In alternative embodiments, the sheath 120, the delivery catheter 140, and/or the inner catheter 160 can be made from metallic materials such as, but not limited to, nitinol, stainless steel, stainless steel alloys, titanium, titanium alloys, and the like, and combinations thereof. In some embodiments, the sheath 120, the delivery catheter 140, and/or the inner catheter 160 can be made from combinations of such polymeric and metallic materials (e.g., polymer layers with metal braid, coil reinforcement, stiffening members, and the like, and combinations thereof).

Figure 6:
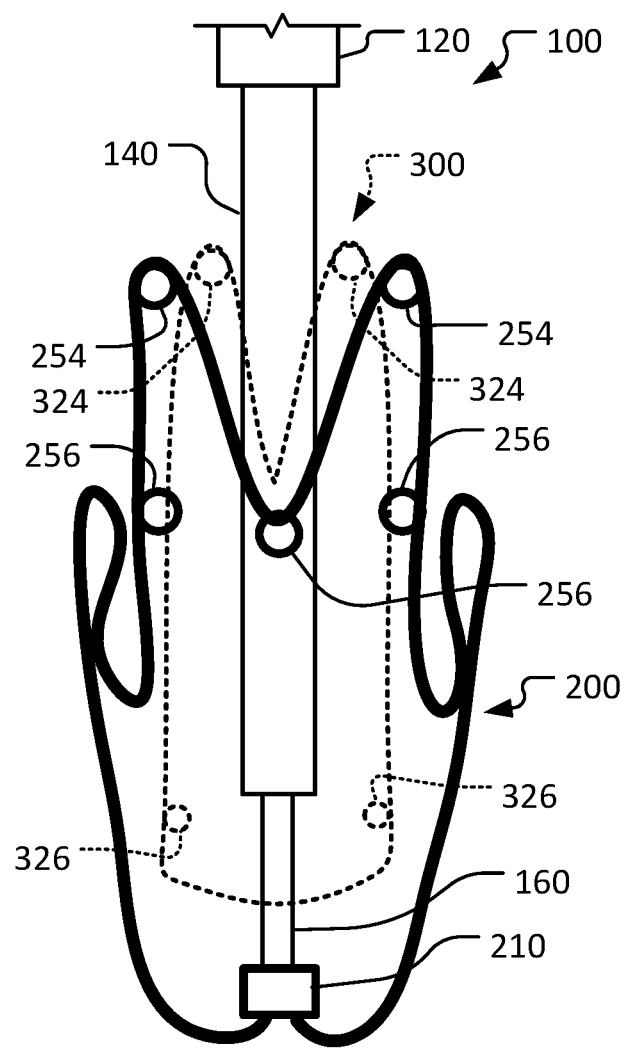
FIG. 6 schematically depicts the nested two-part prosthetic valve as in FIG. 5, with the addition of control wire coupling locations on the anchor assembly and on the valve assembly.

Referring to FIG. 6, in some embodiments one or more control wires can be used to releasably couple the anchor assembly 200 and the valve assembly 300 to the delivery catheter 140. Such control wires can also be used by a clinician to control the radial expansion of the anchor assembly 200 and the valve assembly 300—in some optional implementations, to control the radial expansion of the anchor assembly 200 independently from the radial expansion of the valve assembly 300 during the deployment procedure. For example, when a control wire is slackened (tension is relaxed) the associated anchor assembly 200 or valve assembly 300 will be allowed to radially self-expand. Conversely, when a control wire is tensioned, the associated anchor assembly 200 or valve assembly 300 will be radially contracted, compressed, or constrained. The control wires may also be thought of as "lassos" because, like a lasso, the control wires function to circumferentially, radially, or diametrically control/constrain the anchor assembly 200 and the valve assembly 300.

Control wires can be releasably coupled around one or more regions of the anchor assembly 200 and the valve assembly 300. For example, control wires can be coupled to a proximal end region, one or more mid-body regions, and/or a distal end region of the anchor assembly 200 and/or the valve assembly 300. In some cases, a single control wire can be coupled to both the anchor assembly 200 and the valve assembly 300. In one such example, a single control wire can be coupled to the proximal end regions of both the anchor assembly 200 and the valve assembly 300. Tensioning the single control wire that is coupled to the proximal end regions of both the anchor assembly 200 and the valve assembly 300 will cause the proximal end regions of both the anchor assembly 200 and the valve assembly 300 to be concurrently radially contracted and constrained. Releasing tension from the single control wire that is coupled to the proximal end regions of both the anchor assembly 200 and the valve assembly 300 will allow the proximal end regions of both the anchor assembly 200 and the valve assembly 300 to concurrently radially expand.

In some cases, a single control wire is coupled to only one of either the anchor assembly 200 or the valve assembly 300. In some such cases, a first control wire can be coupled to one region of either the anchor assembly 200 or the valve assembly 300, and a second control wire can be coupled to another region of same anchor assembly 200 or valve assembly 300.

In the depicted embodiment, the anchor assembly 200 is configured to be releasably coupled with a proximal end region control wire at one or more anchor assembly proximal end coupling sites 254. In addition, the anchor assembly 200 is configured to be releasably coupled with a mid-body region control wire at one or more anchor assembly mid-body coupling sites 256.

In the depicted embodiment, the valve assembly 300 is configured to be releasably coupled with a proximal end region control wire at one or more valve assembly proximal end coupling sites 324. In addition, the valve assembly 300 is configured to be releasably coupled with a distal end region control wire at one or more valve assembly distal end coupling sites 326.

The control wire coupling sites (e.g., the anchor assembly proximal end coupling sites 254, the anchor assembly mid-body coupling sites 256, the valve assembly proximal end coupling sites 324, and the valve assembly distal end coupling sites 326) can be various types of structures to which a wire can be releasably coupled. For example, in some embodiments the control wire coupling sites can be a loop of suture material, two loops of suture material, or three or more loops of suture material. In some embodiments, the control wire coupling sites can be a structure defining an eyelet formed by, or attached to, the framework of the anchor assembly 200 and/or the valve assembly 300. In some embodiments, the control wire coupling sites can be cells or struts of the framework of the anchor assembly 200 and/or the valve assembly 300. Other types of suitable control wire coupling sites can also be used.

Referring to FIG. 7, one or more control wires can releasably couple the valve assembly 300 to the delivery catheter 140 (for enhanced clarity, the control wires coupling the anchor assembly 200 to the delivery catheter 140 are not shown). In the depicted embodiment, the valve assembly 300 is coupled to the delivery catheter 140 by: (i) a valve assembly proximal end control wire 142 and (ii) a valve assembly distal end control wire 144. The valve assembly proximal end control wire 142 can be releasably coupled with the valve assembly proximal end coupling sites 324. The valve assembly distal end control wire 144 can be releasably coupled with the valve assembly distal end coupling sites 326.

Referring to FIG. 8, one or more control wires can releasably couple the anchor assembly 200 to the delivery catheter 140 (for enhanced clarity, the control wires coupling the valve assembly 300 to the delivery catheter 140 are not shown). In the depicted embodiment, the anchor assembly 200 is coupled to the delivery catheter 140 by: (i) an anchor assembly proximal end control wire 146 and (ii) an anchor assembly mid-body control wire 148. The anchor assembly proximal end control wire 146 can be releasably coupled with the anchor assembly proximal end coupling sites 254. The anchor assembly mid-body control wire 148 can be releasably coupled with the anchor assembly mid-body coupling sites 256.

Referring to FIG. 9, all four of the aforementioned control wires (the valve assembly proximal end control wire 142, the valve assembly distal end control wire 144, the anchor assembly proximal end control wire 146, and the anchor assembly mid-body control wire 148) are now depicted.

In some implementations, fewer than four control wires are included. For example, in some implementations the anchor assembly mid-body control wire 148 is not included (but the valve assembly proximal end control wire 142, the valve assembly distal end control wire 144, and the anchor assembly proximal end control wire 146), for a total of three control wires. In another example, the proximal ends of the anchor assembly 200 and the valve assembly 300 can share a single control wire, and the valve assembly distal end control wire 144 can be also used, for a total of two control wires. In another example, the proximal ends of the anchor assembly 200 and the valve assembly 300 can share a single control wire, and the valve assembly distal end control wire 144 and the anchor assembly mid-body control wire 148 can be also used, for a total of three control wires.

In some implementations, a deployment control handle/system (such as the deployment frame system 6 of FIG. 1) is used to control the movements of the control wires, and by extension, the movements of the corresponding anchor assembly 200 or valve assembly 300 to which the control wires are coupled. For example, the tension of the control wires can be increased or decreased to thereby allow radial self-expansion, or to thereby cause radial contraction/constriction, of the corresponding anchor assembly 200 or valve assembly 300.

In some embodiments, the control wires extend through lumens defined in the wall of a catheter, such as the delivery catheter 140. The control wires can extend from such lumens through luminal orifices at the end of the catheter, or at non-end luminal orifice locations along the catheter. For example, in the depicted embodiment, the valve assembly distal end control wire 144 extends from luminal orifices at the end of the delivery catheter 140. However, the valve assembly proximal end control wire 142, the anchor assembly proximal end control wire 146, and the anchor assembly mid-body control wire 148 each extend from non-end luminal orifices located along the delivery catheter 140.

In some embodiments, such as the depicted embodiment, individual control wires form a loop at the end of the catheter (e.g., the delivery catheter 140). That is, the control wire exits from a first luminal orifice of the catheter, then loops through one or more attachment sites of the anchor assembly 200 and/or the valve assembly 300, then reenters a second luminal orifice of the catheter. Portions of the control wire are slidably positioned within lumens within the wall of the catheter. The two terminal ends of the control wire can be positioned at the user control mechanism (e.g., the deployment frame system 6 of FIG. 1). To remove a control wire from engagement with the anchor assembly 200 and/or the valve assembly 300, a clinician can simply pull on one end of the control wire while allowing the second end of the control wire to freely pass into the catheter wall lumen. As the clinician continues to pull, the entire control wire can be removed from engagement with the anchor assembly 200 and/or the valve assembly 300, and even from within the lumens of the catheter (if so desired).

While the depicted example includes four control wires (e.g., the valve assembly proximal end control wire 142, the valve assembly distal end control wire 144, the anchor assembly proximal end control wire 146, and the anchor assembly mid-body control wire 148) in some embodiments fewer than four or more than four control wires can be used in conjunction with the depicted nested arrangement of the anchor assembly 200 and valve assembly 300. For example, in some embodiments exactly three control wires are included to couple the nested anchor assembly 200 and valve assembly 300 to the delivery catheter 140. In a first example using three control wires, a first control wire can be releasably coupled with a proximal end region of the valve assembly 300, a second control wire can be releasably coupled with a distal end region of the valve assembly 300, and a third control wire can be releasably coupled with a proximal end region of the anchor assembly 200. In such a case, the relative positioning of the inner catheter 160 (coupled to the hub 210) compared to the delivery catheter 140 can be adjusted to provide some control of the expansion of the mid-body of the anchor assembly 210. For example, extending the inner catheter 160 further distally in comparison to the delivery catheter 140 can cause a radial contraction of the mid-body region of the anchor assembly 200. Conversely, pulling the inner catheter 160 further proximally in comparison to the delivery catheter 140 can cause or allow a radial expansion of the mid-body region of the anchor assembly 200. In a second example using three control wires, a first control wire can be releasably coupled with a distal end region of the valve assembly 300, a second control wire can be releasably coupled with a mid-body region of the anchor assembly 300, and a third control wire can be releasably coupled with the proximal end regions of both of the anchor assembly 200 and the valve assembly 300. That is, a single control wire can be releasably coupled with the proximal end region of the anchor assembly 200 and also with the proximal end region of the valve assembly 300.

While the depicted example includes four control wires (e.g., the valve assembly proximal end control wire 142, the valve assembly distal end control wire 144, the anchor assembly proximal end control wire 146, and the anchor assembly mid-body control wire 148), in some embodiments, exactly two control wires are included to couple the nested anchor assembly 200 and valve assembly 300 to the delivery catheter 140. In one such example, a first control wire can be releasably coupled with a distal end region of the valve assembly 300, and a second control wire can be releasably coupled with the proximal end regions of both of the anchor assembly 200 and the valve assembly 300. That is, a single control wire can be releasably coupled with the proximal end region of the anchor assembly 200 and also with the proximal end region of the valve assembly 300.

Figure 15:
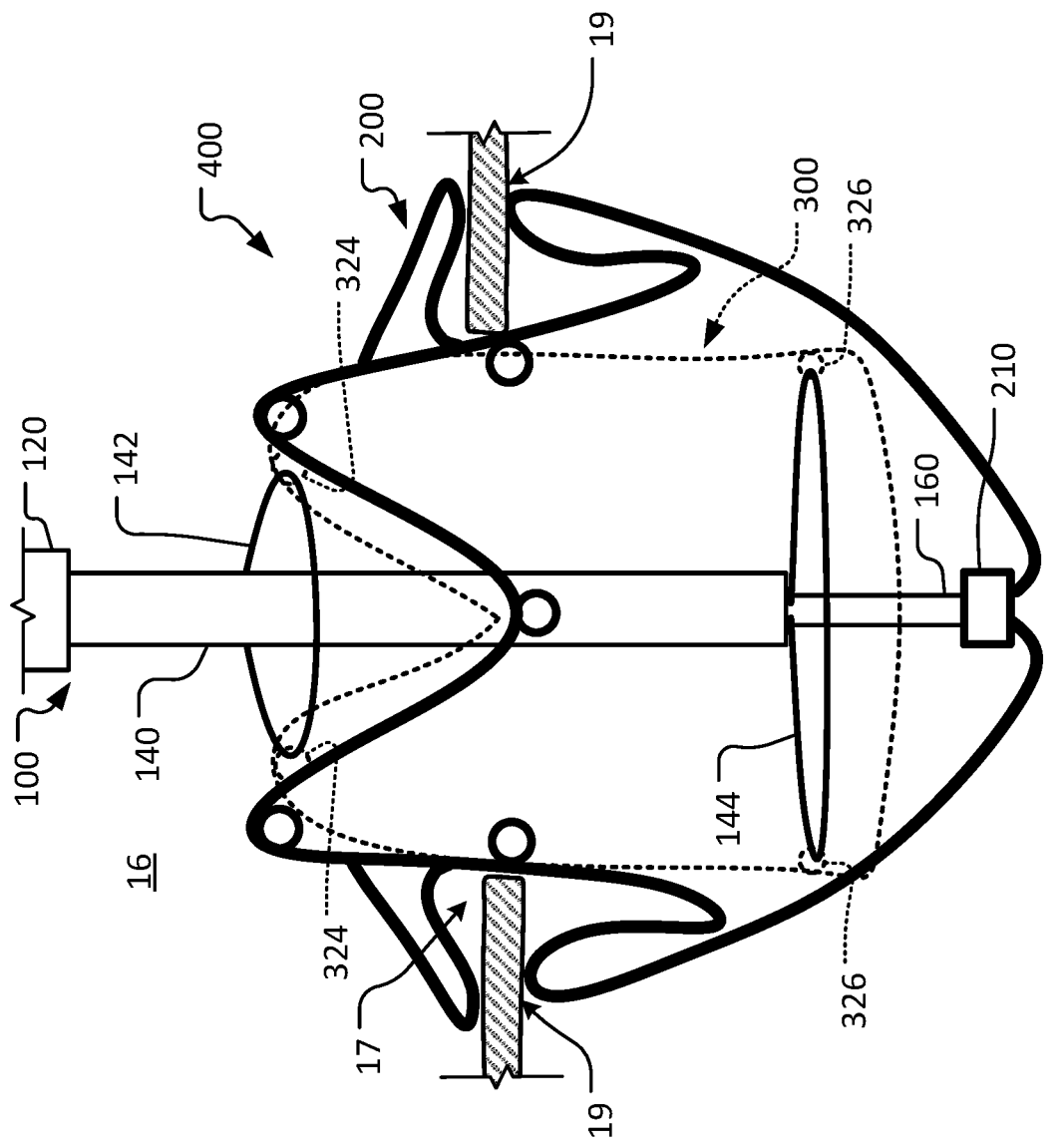
FIG. 15 schematically depicts the nested two-part prosthetic valve with the valve assembly fully expanded and coupled within the anchor assembly that is fully expanded and engaged with the native heart valve.
Figure 16:
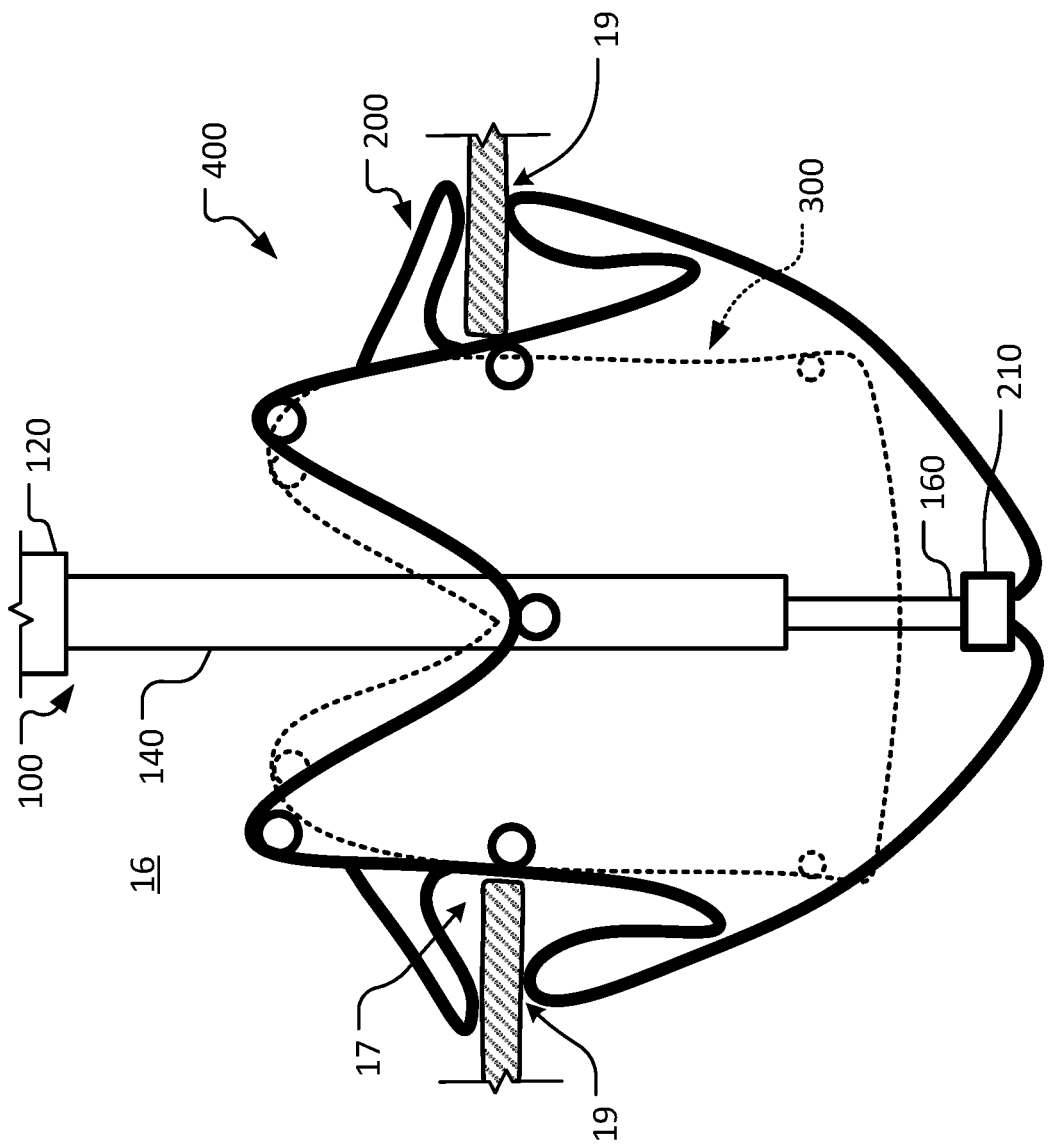
FIG. 16 schematically depicts the nested two-part prosthetic valve as in FIG. 15, with the valve assembly control wires removed.

FIGS. 10-13 schematically depict an example serial process for deploying the anchor assembly 200 in a native heart valve 17 while the anchor assembly 200 and the valve assembly 300 (collectively the two-part prosthetic mitral valve 400; FIGS. 3 and 4) are positioned relative to each other in the nested arrangement. FIGS. 15-17 schematically depict an example serial process for deploying the valve assembly 300 in the native heart valve 17 while the anchor assembly 200 and the valve assembly 300 are positioned relative to each other in the nested arrangement. It should be understood that retrieval of the anchor assembly 200 and/or the valve assembly 300 can be readily performed at any time during the depicted sequential procedures as long as at least one of the control wires remain coupled to the valve assembly 300.

As described elsewhere herein, while the depicted implementation includes four control wires, in some implementations a total of three control wires or a total of two control are included. For those implementations that include a single control wire that is shared by the proximal ends of the anchor assembly 200 and the valve assembly 300, retrieval can be performed, for example, using the following procedure. The anchor assembly mid-body control wire 148 can be released and/or removed from engagement with the anchor assembly 200. Then, the valve assembly distal end control wire 144 can be tensioned to collapse the distal end of the valve assembly 300. Next, the single control wire that is shared by the proximal ends of the anchor assembly 200 and the valve assembly 300 can be tensioned to collapse the proximal end of the valve assembly 300 such that retrieval features (e.g., hooks, clips, slots, etc.) on the delivery catheter 140 become engaged with the framework of the valve assembly 300. Then, the single control wire that is shared by the proximal ends of the anchor assembly 200 and the valve assembly 300 can be released/removed to decouple the collapsed valve assembly 300 from the anchor assembly 200 (while the proximal end of the valve assembly 300 remains engaged with the delivery catheter 140 by virtue of the proximally-located retrieval features and valve assembly distal end control wire 144). Next, the valve assembly 300 can be retracted into sheath 120 (e.g., by pulling the delivery catheter 140 proximally in relation to the sheath 120). The retrieval features on the delivery catheter 140 (with which the valve assembly 300 are engaged) and the tensioned valve assembly distal end control wire 144 facilitate the insertion of the valve assembly 300 (along with the delivery catheter 140) into the sheath 120. Finally, the anchor assembly 200 can be positioned within the sheath 120 by pulling the inner catheter 160 (to which the hub 210 is coupled) into the sheath 120. The anchor assembly 200 may evert as it is pulled into the sheath 120.

Figure 10:
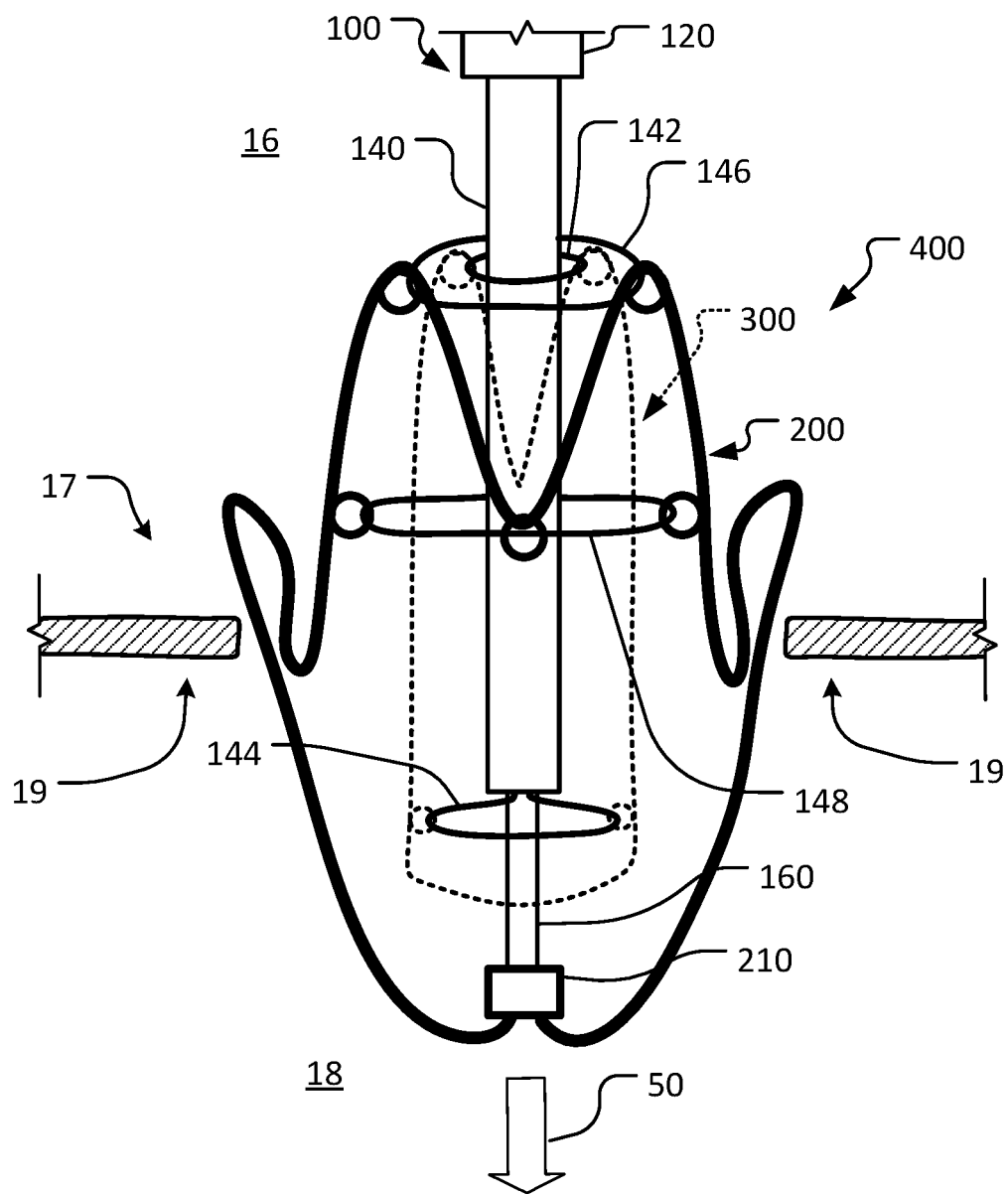
FIG. 10 schematically depicts the nested two-part prosthetic valve as in FIG. 9, with the anchor assembly partially expanded and positioned partially within the annulus of a native heart valve.

Referring to FIG. 10, as described above the transcatheter delivery system 100 can be been used to intravascularly navigate the two-part prosthetic mitral valve 400 to the left atrium 16. The anchor assembly 200 and the valve assembly 300 (positioned relative to each other in the nested arrangement as shown) can be simultaneously expressed from the sheath 120 while in the left atrium 16. In some implementations, it is desirable to orient (e.g., laterally pivot, pan, steer, etc.) the nested anchor assembly 200 and valve assembly 300 within the atrium 16 so that their longitudinal axes are generally perpendicular to the native mitral valve 17, and coaxial with the native mitral valve 17 (e.g., to center the nested anchor assembly 200 with the line of coaptation of the mitral valve 17). Such orienting of the partially or fully expanded nested anchor assembly 200 and valve assembly 300 within the atrium 16 may be advantageous versus having to orient them while they are still constrained within the delivery sheath 120, as the latter assembly can be a relatively large and stiff catheter assembly.

After the nested anchor assembly 200 and valve assembly 300 is expressed from the sheath 120 in the left atrium 16, a clinician can relax some tension from the anchor assembly mid-body control wire 148 to allow the anchor assembly 200 to partially expand. For example, in some cases the mid-body region of the anchor assembly 200 may be allowed to expand about 75% of its fully expanded radial size. Accordingly, the anchor feet 220a, 220b, 220c, and 220d (FIG. 3) expand radially outward. Such expansion can be performed in preparation for seating the anchor feet 220a, 220b, 220c, and 220d within the sub-annular gutter 19 of the native mitral valve 17. At this stage, the other control wires (e.g., the valve assembly proximal end control wire 142, the valve assembly distal end control wire 144, and the anchor assembly proximal end control wire 146) can remain fully tensioned such that the proximal end region of the anchor assembly 200 and the entirety of the valve assembly 200 remain radially contracted.

With the mid-body region of the anchor assembly 200 partially expanded, the nested anchor assembly 200 and valve assembly 300 can be pushed distally as indicated by arrow 50. The anchor feet 220a, 220b, 220c, and 220d may physically help to proper align the anchor assembly 200 to the native mitral valve 17 as the anchor assembly 200 is partially pushed through the annulus of the native mitral valve 17. The distal portions of the nested anchor assembly 200 and valve assembly 300 will pass through the annulus of the mitral valve 17 and into the left ventricle 18 as shown. With the anchor assembly 200 partially radially contracted in a desired orientation, and appropriately aligned with the mitral valve 17, the anchor assembly 200 can be safely passed through the native mitral valve 17 without damaging the native mitral valve 17 and/or entangling chordae tendineae of the mitral valve 17.

Figure 11:
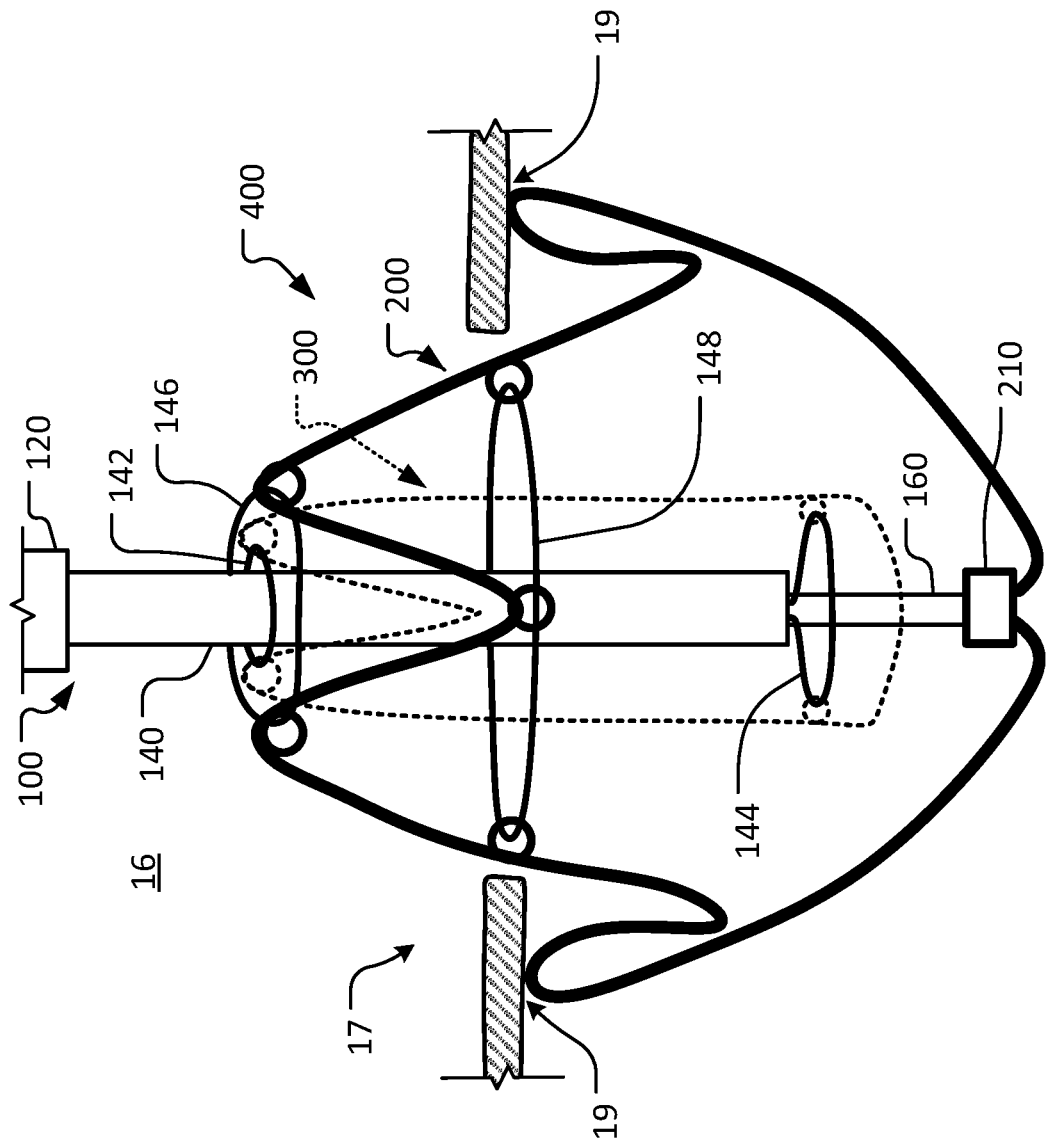
FIG. 11 schematically depicts the nested two-part prosthetic valve as in FIG. 9, with the anchor assembly expanded further than in FIG. 10 and with the anchor feet positioned within a sub-annular gutter of the native valve.

Referring to FIG. 11, further distal movement of the nested anchor assembly 200 and valve assembly 300 will cause the anchor feet 220a, 220b, 220c, and 220d (FIG. 3) to pass through the annulus of the native mitral valve 17 and into the left ventricle 18. Then, the clinician can fully relax (or nearly fully relax) the tension from the anchor assembly mid-body control wire 148 to allow the mid-body region of the anchor assembly 200 to fully expand (or nearly fully expand). Accordingly, the anchor feet 220a, 220b, 220c, and 220d can be then properly seated within the sub-annular gutter 19 of the native mitral valve 17.

The regions at or near the high collagen annular trigones of the sub-annular gutter 19 can generally be relied upon to provide strong, stable anchoring locations. The muscle tissue in the regions at or near the trigones also provides a good tissue ingrowth substrate for added stability and migration resistance of the anchor assembly 200. Therefore, the regions at or near the trigones define a left anterior anchor zone and a right anterior anchor zone. The left anterior anchor zone and the right anterior anchor zone provide advantageous target locations for placement of the lateral anterior foot 220a and the medial anterior foot 220d respectively. The left posterior anchor zone and the right anterior anchor zone of the sub-annular gutter 19 can receive the lateral posterior foot 220b and the medial posterior foot 220c respectively.

Figure 12:
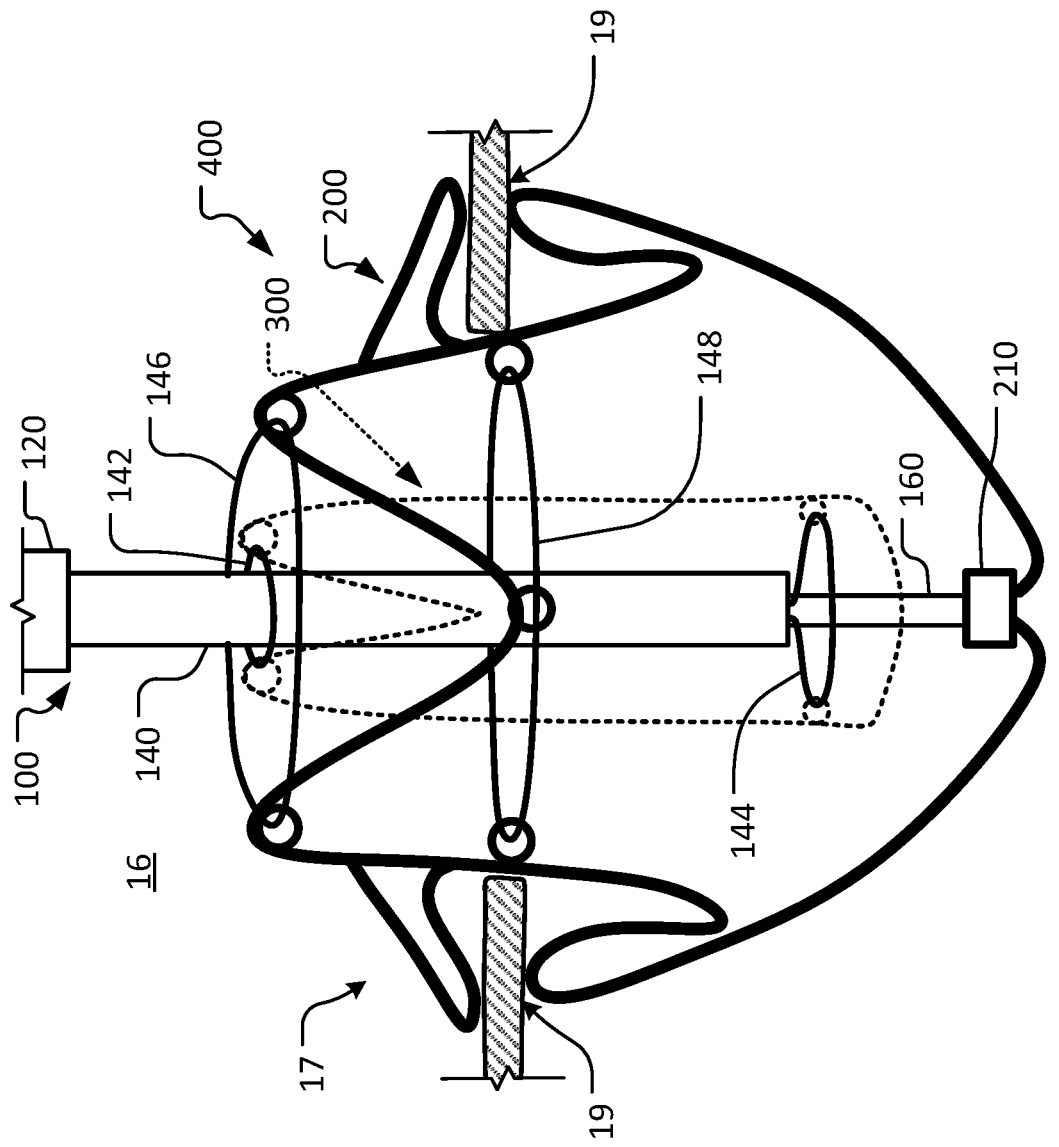
FIG. 12 schematically depicts the nested two-part prosthetic valve as in FIG. 11, with the anchor assembly fully expanded such that the atrial holding features are supra-annularly adjacent to the native valve tissue.

Referring to FIG. 12, as a next step of the process for implanting the two-part prosthetic mitral valve 400 arranged in the nested configuration, the clinician can relax the anchor assembly proximal end control wire 146. Doing so will allow the proximal end of the anchor assembly 200, including the supra-annular structures of the anchor assembly 200, to self-expand. For example (referring also to FIG. 3), relaxing the tension on the anchor assembly proximal end control wire 146 will allow radial expansion of the atrial holding features 240a, 240b, and 240c. The atrial holding features 240a, 240b, and 240c are configured to contact the shelf-like supra-annular tissue surface above the annulus of the mitral valve 17, and to thereby stabilize the anchor assembly 200 in supra-annular areas while providing resistance against migration in the direction towards the left ventricle 18. Relaxing the tension on the anchor assembly proximal end control wire 146 will also allow radial expansion of the lateral anterior anchor arch 250a, the posterior anchor arch 250b, and the medial anterior anchor arch 250c. The lateral anterior anchor arch 250a, the posterior anchor arch 250b, and the medial anterior anchor arch 250c are joined with each other to form the undulating supra-annular ring 250 that acts as a supra-annular structural element for the anchor assembly 200.

With the tensions from the anchor assembly proximal end control wire 146 and the anchor assembly mid-body control wire 148 removed, the anchor assembly 200 is fully expanded and engaged with the native mitral valve 17. Thereafter, the clinician can remove the anchor assembly proximal end control wire 146 and the anchor assembly mid-body control wire 148 from engagement with the anchor assembly 200 if so desired. To do so, the clinician can simply pull on a first end of the control wire 146 and/or 148 while the second end of the control wire 146 and/or 148 is free to move.

Figure 13:
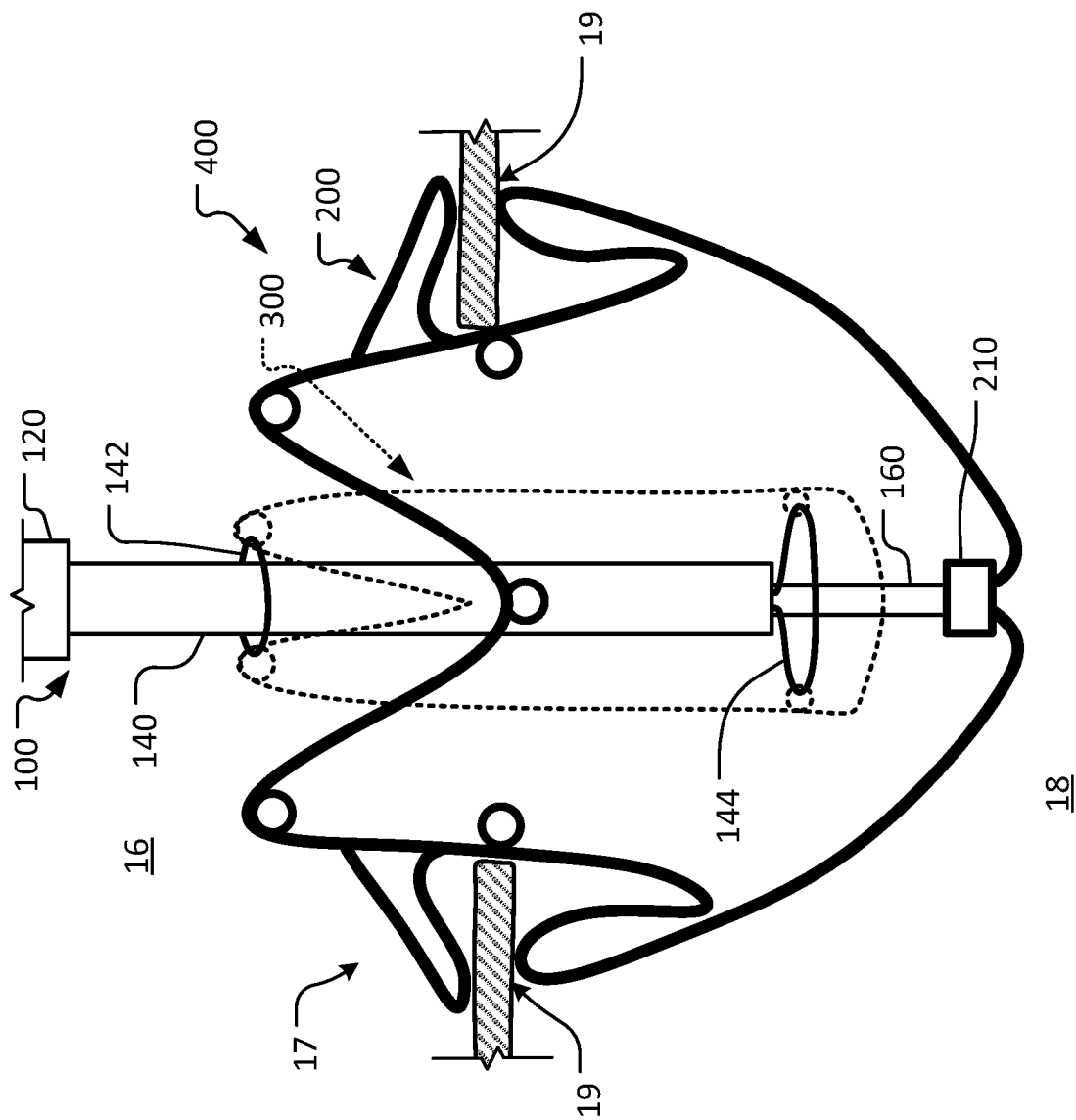
FIG. 13 schematically depicts the nested two-part prosthetic valve as in FIG. 12, with the anchor assembly control wires removed.

Referring to FIG. 13, after a sufficient amount of pulling the control wires 146 and/or 148 by the clinician, the control wire 146 and/or 148 will become disengaged from the anchor assembly 200 as shown. In result, the anchor assembly 200 is fully expanded and engaged with the anatomical structure of the native mitral valve 17. At this stage, the inner catheter 160 can continue to be coupled with the hub 210 of the anchor assembly 200. Therefore, retrieval of the anchor assembly 200 is still possible even though the control wires 146 and 148 have been removed from engagement with the anchor assembly 200.

Figure 14:
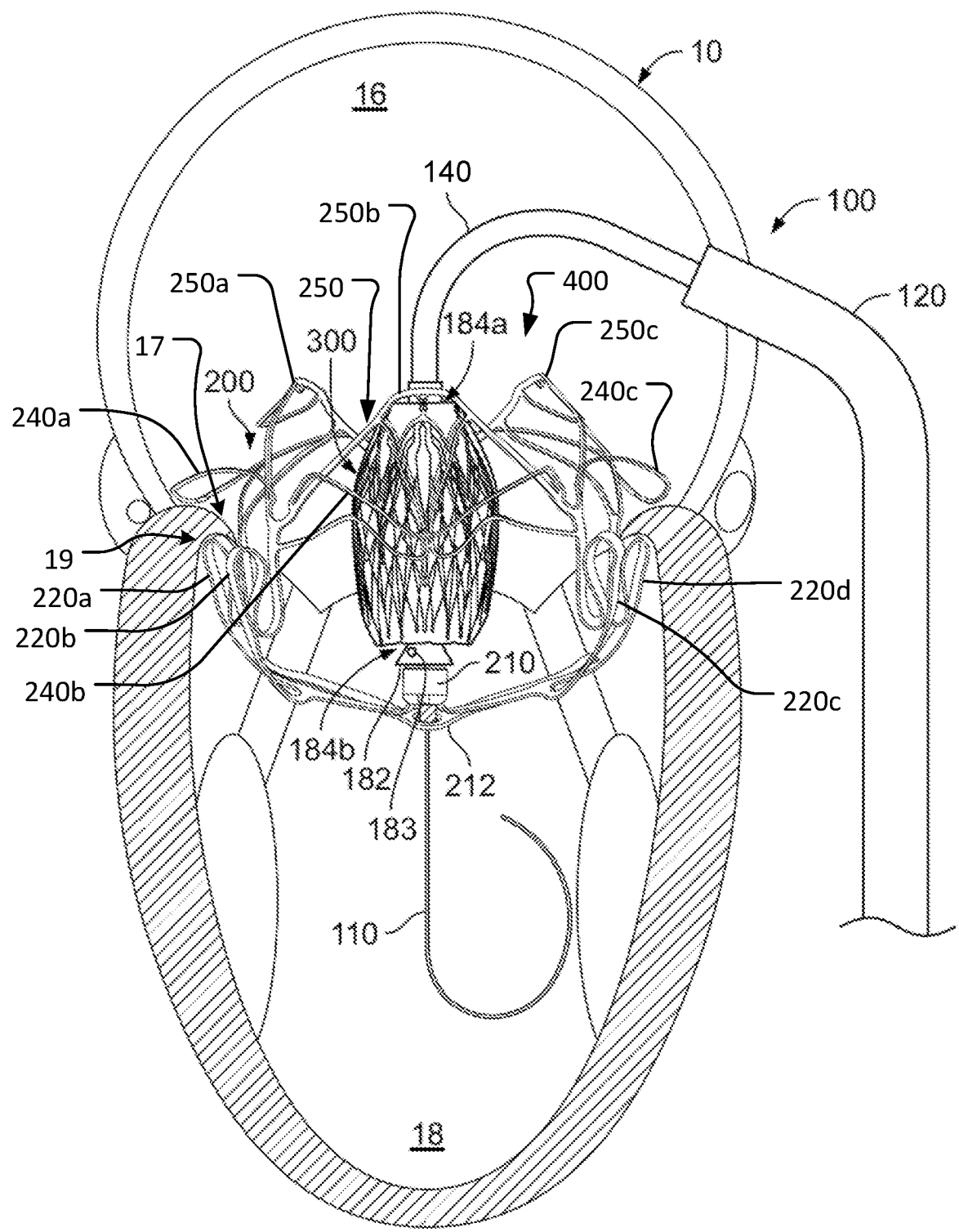
FIG. 14 shows a commissural cross-sectional view of a human heart (from the left side of the heart) and the nested two-part prosthetic valve with the anchor assembly fully deployed within the native mitral valve (as schematically depicted in FIG. 13). The valve assembly is still diametrically constrained to the delivery catheters using control wires.

FIG. 14 illustrates the same arrangement as in FIG. 13, but in a less schematic fashion. For example, the still radially-constrained valve assembly 300 is shown within the expanded anchor assembly 200 that is engaged with the native mitral valve 17. This commissural cross-sectional view of the heart 10 is a cross-sectional view taken through the mitral valve 17 along a plane through the left atrium 16 and left ventricle 18 that is parallel to the line that intersects the two commissures of the mitral valve 17. The view is slightly tilted so that better visualization of the two-part prosthetic mitral valve 400 is provided.

The supra-annular structures of the anchor assembly 200 are radially expanded (e.g., the atrial holding features 240a, 240b, and 240c, and the anchor arches 250a, 250b, and 250c). The atrial holding features 240a, 240b, and 240c are in contact with or adjacent to the shelf-like supra-annular tissue surface above the annulus of the mitral valve 17. The lateral anterior anchor arch 250a, the posterior anchor arch 250b, and the medial anterior anchor arch 250c are expanded to form the undulating supra-annular ring 250 that acts as a supra-annular structural element for the anchor assembly 200.

The sub-annular structures of the anchor assembly 200 are also radially expanded (e.g., the anchor feet 220a, 220b, 220c, and 220d). In this arrangement, the anchor feet 220a, 220b, 220c, and 220d are properly seated within the sub-annular gutter 19 of the native mitral valve 17.

Referring to FIG. 15, a schematic depiction of the two-part prosthetic mitral valve 400 arranged in the nested configuration can once again be used to describe the remaining steps of the deployment process. The anchor assembly 200 is already deployed at this stage (other than the continued releasable coupling of the inner catheter 160 to the hub 210 of the anchor assembly 200).

To allow the valve assembly 300 to radially expand while being nested within the anchor assembly 200, the tensions of the valve assembly proximal end control wire 142 and the valve assembly distal end control wire 144 can be relaxed. Relaxing tension from the valve assembly proximal end control wire 142 and the valve assembly distal end control wire 144 allow the valve assembly 300 to self-expand and to couple with the anchor assembly 200.

In some cases, the tensions of the valve assembly proximal end control wire 142 and the valve assembly distal end control wire 144 can be relaxed simultaneously. In some cases, the tensions of the valve assembly proximal end control wire 142 and the valve assembly distal end control wire 144 can be relaxed serially (including any and all possible patterns of alternating, step-wise, and partial relaxations of the tensions).

When the valve assembly 300 and the anchor assembly 200 are coupled together, the valve assembly 300 is geometrically interlocked within the interior space of the anchor assembly 200 (e.g., in some embodiments by virtue of the tapered shape of the valve assembly 300 within the supra-annular ring and interior space of the anchor assembly 200). In particular, in some embodiments the valve assembly 300 is contained within the interior space between the supra-annular ring 250 and the sub-annular support arms 230a, 230b, 230c, and 230d (refer to FIG. 3).

Referring also to FIG. 16, the next step of the process for deploying the two-part prosthetic mitral valve 400 arranged in the nested configuration can include removal of the valve assembly proximal end control wire 142 from engagement with the valve assembly proximal end coupling sites 324, and removal of the valve assembly distal end control wire 144 from engagement with the valve assembly distal end coupling sites 326. The removals of the valve assembly proximal end control wire 142 and the valve assembly distal end control wire 144 can be performed as described above in reference to the anchor assembly proximal end control wire 146 and the anchor assembly mid-body control wire 148.

After the valve assembly 300 has been expanded into a coupled relationship with the anchor assembly 200, the clinician can verify that the anchor assembly 200 and the valve assembly 300 are in the desired positions. Additionally, the clinician may verify other aspects such as, but not limited to, the hemodynamic performance and sealing of the anchor assembly 200 and the valve assembly 300.

The anchor assembly 200 and the valve assembly 300 are deployed at this stage (other than the continued releasable coupling of the inner catheter 160 to the hub 210 of the anchor assembly 200).

Referring also to FIG. 17, the process of deploying the two-part prosthetic mitral valve 400 arranged in the nested configuration can be completed by disengaging the inner catheter 160 from the hub 210 of the anchor assembly 200, and removing the delivery system 100 from the patient. The SAM containment member 212 (FIG. 3) may also be deployed as a result of this step. The two-part prosthetic mitral valve 400 engaged with the native mitral valve 17 is thereafter able to take over the performance the native mitral valve function.

While the components of the delivery system 100 and the two-part prosthetic mitral valve 400 are depicted in particular relative orientations and arrangements, it should be understood that the depictions are non-limiting.

A number of embodiments of the invention have been described. Nevertheless, it will be understood that various modifications may be made without departing from the scope of the invention. Accordingly, other embodiments are within the scope of the following claims.

What is claimed is:

1. A transcatheter mitral valve replacement system for a heart, comprising:
   a delivery sheath having a distal end portion insertable into a left atrium;
   a delivery catheter slidably disposed within the delivery sheath; and
   a two-part prosthetic mitral valve coupled to the delivery catheter by one or more control wires, the two-part prosthetic mitral valve configured to be disposed within the delivery sheath in a radially compressed condition and to radially self-expand when the two-part prosthetic mitral valve is outside of the delivery sheath and is unconstrained by the one or more control wires, the two-part prosthetic mitral valve comprising:
      a valve assembly including an expandable valve frame and a tri-leaflet occluder; and
      an anchor assembly separately expandable from the valve assembly and defining an interior space within which the valve assembly is nested while the two-part prosthetic mitral valve is within the delivery sheath for simultaneous deployment from the delivery sheath,
      wherein the valve assembly and the anchor assembly are separable from one another, such that the valve assembly and the anchor assembly are separable valve and anchor assemblies simultaneously coupled to the delivery catheter by the one or more control wires while the valve assembly is nested in the anchor assembly, and
   wherein the one or more control wires includes a first control wire coupled to first eyelets on a proximal end portion of the anchor assembly and to second eyelets on a proximal end portion of the valve assembly.

2. The system of claim 1, further comprising:
   a pusher catheter slidably disposed within the delivery catheter and releasably coupled to the anchor assembly.

3. The system of claim 1, wherein the one or more control wires comprises:
   a second control wire coupled to a mid-body portion of the anchor assembly; and
   a third control wire coupled to a distal end portion of the valve assembly.

4. The system of claim 1, wherein the one or more control wires comprises a second control wire coupled to a distal end portion of the valve assembly.

5. The system of claim 1, wherein the one or more control wires comprises a second control wire coupled to a mid-body portion of the anchor assembly.

6. The system of claim 1, wherein a mid-body portion of the valve assembly has a D-shaped cross-sectional shape.

7. The system of claim 1, wherein the anchor assembly comprises four feet configured to reside within a sub-annular gutter of a native mitral valve when the two-part prosthetic mitral valve is implanted within the heart.

8. The system of claim 7, wherein the anchor assembly comprises supra-annular features including an undulating supra-annular ring that defines an end of the interior space and atrial holding features configured to contact supra-annular tissue surfaces above an annulus of the native mitral valve.

9. The system of claim 1, further comprising a deployment control system coupled to proximal ends of the delivery sheath and the delivery catheter.

10. The system of claim 1, wherein the anchor assembly includes an expandable anchor frame defining the interior space and defining a plurality of sub-annular anchor feet, wherein the anchor assembly is expandable from a compressed anchor delivery configuration to an expanded anchor deployment configuration in which the sub-annular anchor feet are sized and shaped to engage along an underside of an annulus of a mitral valve.

11. The system of claim 10, wherein the expandable valve frame is separately expandable from the expandable anchor frame and being nested within the interior space of the expandable anchor frame while the anchor assembly is in the compressed anchor delivery configuration, wherein the expandable valve frame defines a central orifice and the tri-leaflet occluder positioned within the central orifice, wherein the valve assembly is expandable from a compressed valve delivery configuration to an expanded valve deployment configuration after the anchor assembly is in the expanded anchor deployment configuration.

12. The system of claim 10, wherein the plurality of sub-annular anchor feet of the anchor assembly comprises four anchor feet configured to reside within a sub-annular gutter of the mitral value when the anchor assembly is in the expanded anchor deployment configuration.

13. The system of claim 10, wherein the anchor assembly comprises a supra-annular element including an undulating supra-annular ring that defines an uppermost end of the interior space and atrial holding elements configured to contact supra-annular tissue above the annulus of the mitral valve.

* * * * *